Patent Number: 4,769,481
… Date of Patent: Sep. 6, 1988

[54] N-CARBAMOYLARYL CARBOXIMIDIC ACID ESTERS, AND THEIR USE AS INSECTICIDES

[75] Inventors: Volker Koch, Kelkheim; Gerhard Burghardt, Hofheim am Taunus, both of Fed. Rep. of Germany

[73] Assignee: Hoechst Aktiengesellschaft, Frankfurt am Main, Fed. Rep. of Germany

[21] Appl. No.: 17,029

[22] Filed: Feb. 18, 1987

Related U.S. Application Data

[63] Continuation of Ser. No. 653,692, Sep. 21, 1984, abandoned.

[30] Foreign Application Priority Data

Sep. 22, 1983 [DE] Fed. Rep. of Germany ....... 3334207

[51] Int. Cl.⁴ .......................................... C07C 119/20
[52] U.S. Cl. ................................................. 558/9
[58] Field of Search ............................................ 558/9

[56] References Cited

U.S. PATENT DOCUMENTS 3,742,000  6/1973  Scanlon et al. .................. 260/453.7
4,431,667  2/1984  Nelson ................................. 558/9

FOREIGN PATENT DOCUMENTS 0005944  3/1983  European Pat. Off. ................. 558/9

OTHER PUBLICATIONS

R. Rogers, Chem. Rev. 61, 179 (1961).
J. Org. Chem., vol. 26, 412 (1961).
Houben Weyl, vol. E 4, 741 837 (1983).
Beilsteins Handbuch der Organischen Chemie, vol. E IV 13, 1208 (1985).
Lichtenberger et al., "On Nucleophilic Additions to Trifluorochloroethylene", Bull. Soc. Chim. Fr., 5th Series, 581-592 (1957).
Kuehle et al., "Fluorodichloromethylthio–Compounds and Their Use in Plant Protection", Angew. Chem., 76, No. 19, 807-816 (1964).

Primary Examiner—Alan L. Rotman
Assistant Examiner—Robert C. Whittenbaugh
Attorney, Agent, or Firm—Curtis, Morris & Safford

[57] ABSTRACT

The compounds of the formula I

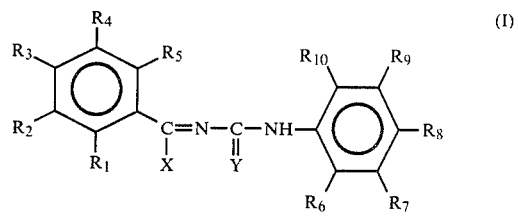

in which
$R_1$ to $R_5$ denote hydrogen; alkyl, alkoxy, alkylmercapto, alkylsulfinyl, alkylsulfonyl, alkylsulfonyloxy each of which can be halogenated, halogen or nitro, $R_6$ to $R_{10}$ denote hydrogen; alkyl, alkoxy, alkenyloxy, alkylmercapto, alkenylmercapto, alkylsulfonyl or $C_3$-hydroxyalkyl each of which can be halogenated, (substituted) benzyloxy, alkoxycarbonyl or NRR', and $R_7$ and $R_8$ together can form a (substituted) alkylenedioxy radical,
X denotes $OR_{11}$ in which $R_{11}$ denotes optionally halogenated alkyl, cycloalkyl, alkenyl or alkynyl or optionally halogenated benzyl, or $SR_{12}$ in which $R_{12}$ denotes alkyl or benzyl each of which can be halogenated, and
Y denotes oxygen or sulfur, subject to the proviso that, if $R_1$ and $R_5$ both denote fluorine and $R_2$, $R_3$ and $R_4$ denote hydrogen, the radicals $R_6$ to $R_{10}$ must not each represent halogenated $(C_1$-$C_6)$-alkyl or halogen, possess an intense action against a broad spectrum of harmful insects.

9 Claims, No Drawings

N-CARBAMOYLARYL CARBOXIMIDIC ACID ESTERS, AND THEIR USE AS INSECTICIDES

This application is a continuation of application Ser. No. 653,692, filed Sept. 21, 1984, abandoned.

It is already known that certain N-carbamoyl-2,6-difluorobenz(thio)carboximidic acid esters have insecticidal properties (European Pat. No. 5,944). There are, however, disadvantages in the use of these, such as insufficient activity.

New substituted N-(thio)carbamoylaryl(thio)carboximidic acid esters having advantageous insecticidal properties have now been found.

The present invention relates, therefore, to the compounds of the formula I

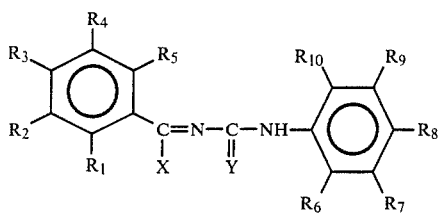

in which $R_1$ to $R_5$ independently of one another denote hydrogen; $(C_1-C_6)$-alkyl, $(C_1-C_6)$-alkoxy, $(C_1-C_6)$-alkylmercapto, $(C_1-C_6)$-alkylsulfinyl, $(C_1-C_6)$-alkylsulfonyl or $(C_1-C_6)$-alkylsulfonyloxy, it being possible for the abovementioned radicals to be monosubstituted or polysubstituted by halogen; or halogen or nitro, $R_6$ to $R_{10}$ independently of one another denote hydrogen; $(C_1-C_6)$-alkyl, $(C_1-C_6)$-alkoxy, $(C_1-C_6)$-alkenyloxy, $(C_1-C_6)$-alkylmercapto, $(C_1-C_6)$-alkenylmercapto, $(C_1-C_6)$-alkylsulfonyl or $C_3$-hydroxyalkyl, it being possible for the abovementioned radicals to be monosubstituted or polysubstituted by halogen; benzyloxy which can be substituted by halogen, $(C_1-C_6)$-halogenoalkyl, $(C_1-C_6)$-halogenoalkoxy, cyano or nitro; $(C_1-C_9)$-alkoxycarbonyl;

NRR' in which R and R' independently of one another denote $(C_1-C_6)$-alkyl, $(C_3-C_6)$-alkenyl or $(C_3-C_6)$-alkynyl, it being possible for these substituents to be monosubstituted or polysubstituted by halogen, or denote halogen, nitro or cyano, or R and R', together with the common nitrogen atom, form a saturated 5-membered ring or 6-membered ring which can contain oxygen, sulfur or NR'' as a ring member and which can be substituted by $(C_1-C_3)$-alkyl, R'' denoting $(C_1-C_3)$-alkyl, and $R_7$ and $R_8$ together can form a $(C_1-C_2)$-alkylenedioxy radical which can be substituted by halogen and $CF_3$, X denotes $OR_{11}$ in which $R_{11}$ denotes optionally halogenated $(C_1-C_6)$-alkyl, $(C_5-C_6)$-cycloalkyl, $(C_3-C_6)$-alkenyl, $(C_3-C_6)$-alkynyl or optionally halogenated benzyl, or X denotes $SR_{12}$ in which $R_{12}$ denotes $(C_1-C_6)$-alkyl or benzyl which can be monosubstituted or polysubstituted by halogen, and Y denotes oxygen or sulfur, subject to the proviso that, if $R_1$ and $R_5$ both denote fluorine and $R_2$, $R_3$ and $R_4$ denote hydrogen, the radicals $R_6$ to $R_{10}$ must not each represent halogenated $((C_1-C_6)$-alkyl or halogen.

The following are examples of compounds, according to the invention, of the formula I:

Ethyl N-[N-(2-fluorophenyl)-carbamoyl]-2,6-difluorobenzcarboximidate

Ethyl N-[N-(2-fluorophenyl)-carbamoyl]-2,6-dimethoxybenzcarboximidate

Ethyl N-[N-(2-ethoxyphenyl)-carbamoyl]-2-fluorobenzcarboximidate

Ethyl N-[N-(3-(1,1,2,2-tetrafluoroethoxy)-phenyl)-carbamoyl]-benzcarboximidate

Ethyl N-[N-(3-nitrophenyl)-carbamoyl]-2,6-difluorobenzcarboximidate

Ethyl N-[N-(3-(nitrophenyl)-carbamoyl]-2-chloro-6-fluorobenzcarboximidate

Ethyl N-[N-(3-(1,1,1,3,3,3-hexafluoro-2-propylamino)-phenyl)-carbamoyl]-2-fluorobenzcarboximidate Ethyl N-[N-(b 3-methoxycarbonylphenyl)-carbamoyl]-2-fluorobenzcarboximidate Ethyl N-[N-(3-difluoromethylphenyl)-carbamoyl]-2-fluorobenzcarboximidate Ethyl N-[N-(3-trifluoromethylphenyl)-carbamoyl]-2-fluorobenzcarboximidate Ethyl N-[N-(3-trifluoromethylphenyl)-carbamoyl]-2,6-difluorobenzcarboximidate Ethyl N-[N-(4-fluorophenyl)-carbamoyl]-2-fluorobenzcarboximidate 2-Propyl N-[N-(4-fluorophenyl)-carbamoyl]-2-chloro-6-fluorobenzcarboximidate Ethyl N-[N-(4-chlorophenyl)-carbamoyl]-benzcarboximidate Propargyl N-[N-(4-chlorophenyl)-carbamoyl]-benzcarboximidate Ethyl N-[N-(4-chlorophenyl)-carbamoyl]-2-fluorobenzcarboximidate Methyl N-[N-(4-chlorophenyl)-carbamoyl]-2-chloro-6-fluorobenzcarboximidate Ethyl N-[N-(4-difluoromethoxyphenyl)-carbamoyl]-2-fluorobenzcarboximidate Ethyl N-[N-(4-difluoromethoxyphenyl)-carbamoyl]-2-chlorobenzcarboximidate Ethyl N-[N-(4-difluoromethoxyphenyl)-carbamoyl]-2,6-difluorobenzcarboximidate Ethyl N-[N-(4-difluoromethoxyphenyl)-carbamoyl]-2-chloro-6-fluorobenzcarboximidate Ethyl N-[N-(4-difluoromethoxyphenyl)-carbamoyl]-2-chloro-4-fluorobenzcarboximidate Ethyl N-[N-(4-difluoromethoxyphenyl)-carbamoyl]-2-chloro-5-fluorobenzcarboximidate Ethyl N-[N-(4-difluoromethoxyphenyl)-carbamoyl]-2,4-dichlorobenzcarboximidate Ethyl N-[N-(4-difluoromethoxyphenyl)-carbamoyl]-2,6-dichlorobenzcarboximidate Ethyl N-[N-(4-chlorodifluoromethoxyphenyl)-carbamoyl]-2-fluorobenzcarboximidate Ethyl N-[N-(4-chlorodifluoromethoxyphenyl)-carbamoyl]-2-chlorobenzcarboximidate Ethyl N-[N-(4-chlorodifluoromethoxyphenyl)-carbamoyl]-2,6-difluorobenzcarboximidate Ethyl N-[N-(4-chlorodifluoromethoxyphenyl)-carbamoyl]-2-chloro-4-fluorobenzcarboximidate Ethyl N-[N-(4-chlorodifluoromethoxyphenyl)-carbamoyl]-2-chloro-5-fluorobenzcarboximidate Ethyl N-[N-(4-chlorodifluoromethoxyphenyl)-carbamoyl]-2,4-dichlorobenzcarboximidate Ethyl N-[N-(4-trifluoromethoxyphenyl)-carbamoyl]-benzcarboximidate Ethyl N-[N-(4-trifluoromethoxyphenyl)-carbamoyl]-2-fluorobenzcarboximidate
Ethyl N-[N-(4-trifluoromethoxyphenyl)-carbamoyl]-2-fluorobenzcarboximidate
1-Propyl N-[N-(4-trifluoromethoxyphenyl)-carbamoyl]-2-fluorobenzcarboximidate
1-Butyl N-[N-(4-trifluoromethoxyphenyl)-carbamoyl]-2-fluorobenzcarboximidate
1-Hexyl N-[N-(4-trifluoromethoxyphenyl)-carbamoyl]-2-fluorobenzcarboximidate
Cyclohexyl N-[N-(4-trifluoromethoxyphenyl)-carbamoyl]-2-fluorobenzcarboximidate
Ethyl N-[N-(4-trifluoromethoxyphenyl)-carbamoyl]-3-fluorobenzcarboximidate
Ethyl N-[N-(4-trifluoromethoxyphenyl)-carbamoyl]-2-chlorobenzcarboximidate
Ethyl N-[N-(4-trifluoromethoxyphenyl)-carbamoyl]-4-chlorobenzcarboximidate
Ethyl N-[N-(4-trifluoromethoxyphenyl)-carbamoyl]-2-iodobenzcarboximidate
Ethyl N-[N-(4-trifluoromethoxyphenyl)-carbamoyl]-2,4-difluorobenzcarboximidate
Ethyl N-[N-(4-trifluoromethoxyphenyl)-carbamoyl]-2,6-difluorobenzcarboximidate
1-Hexyl N-[N-(4-trifluoromethoxyphenyl)-carbamoyl]-2,6-difluorobenzcarboximidate
Ethyl N-[N-(4-trifluoromethoxyphenyl)-carbamoyl]-4-chloro-2-fluorobenzcarboximidate
Ethyl N-[N-(4-trifluoromethoxyphenyl)-carbamoyl]-5-chloro-2-fluorobenzcarboximidate
Ethyl N-[N-(4-trifluoromethoxyphenyl)-carbamoyl]-2-chloro-6-fluorobenzcarboximidate
Ethyl N-[N-(4-trifluoromethoxyphenyl)-carbamoyl]-2-chloro-4-fluorobenzcarboximidate
Ethyl N-[N-(4-trifluoromethoxyphenyl)-carbamoyl]-2-chloro-5-fluorobenzcarboximidate
Ethyl N-[N-(4-trifluoromethoxyphenyl)-carbamoyl]-2,4-dichlorobenzcarboximidate
Ethyl N-[N-(4-trifluoromethoxyphenyl)-carbamoyl]-2,5-dichlorobenzcarboximidate
Ethyl N-[N-(4-trifluoromethoxyphenyl)-carbamoyl]-2,6-dichlorobenzcarboximidate
Ethyl N-[N-(4-trifluoromethoxyphenyl)-carbamoyl]-pentafluorobenzcarboximidate
Ethyl N-[N-(4-trifluoromethoxyphenyl)-carbamoyl]-2-chloro-6-methoxybenzcarboximidate
Ethyl N-[N-(4-trifluoromethoxyphenyl)-carbamoyl]-2-fluoro-5-nitrobenzcarboximidate
Ethyl N-[N-(4-trifluoromethoxyphenyl)-carbamoyl]-2-chloro-5-nitrobenzcarboximidate
Ethyl N-[N-(4-trifluoromethoxyphenyl)-carbamoyl]-2-methanesulfonyloxybenzcarboximidate
Ethyl N-[N-(4-trifluoromethoxyphenyl)-carbamoyl]-2-difluoromethoxybenzcarboximidate
Ethyl N-[N-(4-trifluoromethoxyphenyl)-carbamoyl]-4-trifluoromethoxybenzcarboximidate
Ethyl N-[N-(4-trifluoromethoxyphenyl)-carbamoyl]-3-trifluoromethoxybenzcarboximidate
Ethyl N-[N-4-trifluoromethoxyphenyl)-carbamoyl]-2-methoxybenzcarboximidate
Ethyl N-[N-(4-trifluoromethoxyphenyl)-carbamoyl]-4-(1,1-difluoro-2,2,2-trichloroethoxy)-benzcarboximidate
Ethyl N-[N-(4-trifluoromethoxyphenyl)-carbamoyl]-2-difluoromethylmercaptobenzcarboximidate
Ethyl N-[N-(4-trifluoromethoxyphenyl)-carbamoyl]-3-nitro-5-trifluoromethylbenzcarboximidate
Ethyl N-[N-(4-trifluoromethoxyphenyl)-carbamoyl]-2-trifluoromethylbenzcarboximidate
Methyl N-[N-(4-trifluoromethoxyphenyl)-carbamoyl]-3-trifluoromethylcarboximidate
Ethyl N-[N-(4-trifluoromethoxyphenyl)-carbamoyl]-2-methylbenzcarboximidate
Propargyl N-[N-(4-(1,1,2,2-tetrafluoroethoxy)-phenyl)-carbamoyl]-benzcarboximidate
2,2,2-Trifluoroethyl N-[N-(4-(1,1,2,2-tetrafluoroethoxy)-phenyl)-carbamoyl]-benzcarboximidate
Ethyl N-[N-(4-(1,1,2,2-tetrafluoroethoxy)-phenyl)-carbamoyl]-2-fluorobenzcarboximidate
Ethyl N-[N-(4-(1,1,2,2-tetrafluoroethoxy)-phenyl)-carbamoyl]-2-chlorobenzcarboximidate
Ethyl N-[N-(4-(1,1,2,2-tetrafluoroethoxy)-phenyl)-carbamoyl]-2,6-difluorobenzcarboximidate
Ethyl N-[N-(4-(2,2-dichloro-1,1-difluoroethoxy)-phenyl)-carbamoyl]-2-fluorobenzcarboximidate
Ethyl N-[N-(4-(2,2-dichloro-1,1-difluoroethoxy)-phenyl)-carbamoyl]-2-chlorobenzcarboximidate
Ethyl N-[N-(4-(2,2-dichloro-1,1-difluoroethoxy)-phenyl)-carbamoyl]-2,6-difluorobenzcarboximidate
Ethyl N-[N-(4-(1,1,2,3,3,3-hexafluoro-1-propoxy)-phenyl)-carbamoyl]-2-fluorobenzcarboximidate
Ethyl N-[N-(4-(1,1,2,3,3,3-hexafluoro-1-propoxy)-phenyl)-carbamoyl]-2-chlorobenzcarboximidate
Ethyl N-[N-(4-(1,1,2,3,3,3-hexafluoro-1-propoxy)-phenyl)-carbamoyl]-2,6-difluorobenzcarboximidate
Ethyl N-[N-(4-(1,1,2,3,3,3-hexafluoro-1-propoxy)-phenyl)-carbamoyl]-2-chloro-4-fluorobenzcarboximidate
Ethyl N-[N-(4-(1,1,2,3,3,3-hexafluoro-1-propoxy)-phenyl)-carbamoyl]-2,4-dichlorobenzcarboximidate
Ethyl N-[N-(4-(1,2-dichloroethenyloxy)-phenyl)-carbamoyl]-2-fluorobenzcarboximidate
Ethyl N-[N-(4-(1,2-dichloroethenyloxy)-phenyl)-carbamoyl]-2-chlorobenzcarboximidate
Ethyl N-[N-(4-(1,2-dichloroethenyloxy)-phenyl)-carbamoyl]-2,6-difluorobenzcarboximidate
Ethyl N-[N-(4-difluoromethylmercaptophenyl)-carbamoyl]-2-fluorobenzcarboximidate
Ethyl N-[N-(4-difluoromethylmercaptophenyl)-carbamoyl]-2-chlorobenzcarboximidate
Ethyl N-[N-(4-difluoromethylmercaptophenyl)-carbamoyl]-2,6-difluorobenzcarboximidate
Ethyl N-[N-(4-chlorodifluoromethylmercaptophenyl)-carbamoyl]-2-fluorobenzcarboximidate
Ethyl N-[N-(4-chlorodifluoromethylmercaptophenyl)-carbamoyl]-2-chlorobenzcarboximidate
Ethyl N-[N-(4-chlorodifluoromethylmercaptophenyl)-carbamoyl]-2,6-difluorobenzcarboximidate
Ethyl N-[N-(4-chlorodifluoromethylmercaptophenyl)-carbamoyl]-4-chloro-2-fluorobenzcarboximidate
Ethyl N-[N-(4-chlorodifluoromethylmercaptophenyl)-carbamoyl]-2-chloro-6-fluorobenzcarboximidate
Ethyl N-[N-(4-chlorodifluoromethylmercaptophenyl)-carbamoyl]-2-chloro-4-fluorobenzcarboximidate
Ethyl N-[N-(4-chlorodifluoromethylmercaptophenyl)-carbamoyl]-2,4-dichlorobenzcarboximidate
Ethyl N-[N-(4-trifluoromethylmercaptophenyl)-carbamoyl]-2-fluorobenzcarboximidate
Ethyl N-[N-(4-trifluoromethylmercaptophenyl)-carbamoyl]-2-chlorobenzcarboximidate
Ethyl N-[N-(4-trifluoromethylmercaptophenyl)-carbamoyl]-2,6-difluorobenzcarboximidate
Ethyl N-[N-(4-trifluoromethylmercaptophenyl)-carbamoyl]-2,4-difluorobenzcarboximidate Ethyl N-[N-(4-trifluoromethylmercaptophenyl)-carbamoyl]-4-chloro-2-fluorobenzcarboximidate
Ethyl N-[N-(4-trifluoromethylmercaptophenyl)-carbamoyl]-2-chloro-4-fluorobenzcarboximidate
Ethyl N-[N-(4-trifluoromethylmercaptophenyl)-carbamoyl]-2-chloro-5-fluorobenzcarboximidate
Ethyl N-[N-(4-trifluoromethylmercaptophenyl)-carbamoyl]-2,6-dichlorobenzcarboximidate
Ethyl N-[N-(4-(1,1,2,2-tetrafluoroethyl)-mercaptophenyl)-carbamoyl]-2-fluorobenzcarboximidate
Ethyl N-[N-(4-(1,1,2,2-tetrafluoroethyl)-mercaptophenyl)-carbamoyl]-2-chlorobenzcarboximidate
Ethyl N-[N-(4-(1,1,2,2-tetrafluoroethyl)-mercaptophenyl)-carbamoyl]-2,6-difluorobenzcarboximidate
Ethyl N-[N-(4-(1,1,2,2-tetrafluoroethyl)-mercaptophenyl)-carbamoyl]-2-chloro-4-fluorobenzcarboximidate
Ethyl N-[N-(4-(1,1,2,2-tetrafluoroethyl)-mercaptophenyl)-carbamoyl]-2,4-dichlorobenzcarboximidate
Ethyl N-[N-(4-(2-chloro-1,1,2-trifluoroethyl)-mercaptophenyl)-carbamoyl]-2-fluorobenzcarboximidate
Ethyl N-[N-(4-(2-chloro-1,1,2-trifluoroethyl)-mercaptophenyl)-carbamoyl]-2-chlorobenzcarboximidate
Ethyl N-[N-(4-(2-chloro-1,1,2-trifluoroethyl)-mercaptophenyl)-carbamoyl]-2,4-difluorobenzcarboximidate
Ethyl N-[N-(4-(2-chloro-1,1,2-trifluoroethyl)-mercaptophenyl)-carbamoyl]-4-chloro-2-fluorobenzcarboximidate
Ethyl N-[N-(4-(2-chloro-1,1,2-trifluoroethyl)-mercaptophenyl)-carbamoyl]-2-chloro-4-fluorobenzcarboximidate
Ethyl N-[N-(4-(2-chloro-1,1,2-trifluoroethyl)-mercaptophenyl)-carbamoyl]-2-chloro-b 5-fluorobenzcarboximidate
Ethyl N-[N-(4-(2-chloro-1,1,2-trifluoroethyl)-mercaptophenyl)-carbamoyl]-5-chloro-2-fluorobenzcarboximidate
Ethyl N-[N-(4-(2-chloro-1,1,2-trifluoroethyl)-mercaptophenyl)-carbamoyl]-2,4-dichlorobenzcarboximidate
Ethyl N-[N-(4-(1,1,2,3,3,3-hexafluoro-1-propyl)-mercaptophenyl)-carbamoyl]-2-fluorobenzcarboximidate
Ethyl N-[N-(4-(1,1,2,3,3,3-hexfluoro-1-propyl)-mercaptophenyl)-carbamoyl]-2-chlorobenzcarboximidate
Ethyl N-[N-(4-(1,1,2,3,3,3-hexafluoro-1-propyl)-mercaptophenyl)-carbamoyl]-2,6-difluorobenzcarboximidate
Ethyl N-[N-(4-(1,1,2,3,3,3-hexafluoro-1-propyl)-mercaptophenyl)-carbamoyl]-2-chloro-4-fluorobenzcarboximidate
Ethyl N-[N-(4-(1,1,2,3,3,3-hexafluoro-1-propyl)-mercaptophenyl)-carbamoyl]-2,4-dichlorobenzcarboximidate
Ethyl N-[N-(4-trifluoromethylsulfonylphenyl)-carbamoyl]-2-fluorobenzcarboximidate
Ethyl N-[N-(4-trifluoromethylsulfonylphenyl)-carbamoyl]-2-chlorobenzcarboximidate
Ethyl N-[N-(4-trifluoromethylsulfonylphenyl)-carbamoyl]-2,6-difluorobenzcarboximidate
Ethyl N-[N-(4-nitrophenyl)-carbamoyl]-2-fluorobenzcarboximidate
Ethyl N-[N-(4-nitrophenyl)-carbamoyl]-2-chlorobenzcarboximidate
Ethyl N-[N-(4-nitrophenyl)-carbamoyl]-2,6-difluorocarboximidate
Ethyl N-[N-(4-nitrophenyl)-carbamoyl]-2-chloro-6-fluorobenzcarboximidate
Ethyl N-[N-(4-nitrophenyl)-carbamoyl]-2,6-dichlorobenzcarboximidate
Ethyl N-[N-(4-trifluorophenyl)-carbamoyl]-2-fluorobenzcarboximidate
Ethyl N-[N-(4-trifluorophenyl)-carbamoyl]-2-chloro-6-fluorobenzcarboximidate
Ethyl N-[N-(4-trifluorophenyl)-carbamoyl]-2,6-dichlorobenzcarboximidate
Ethyl N-[N-(4-(1,1,1,3,3,3-hexafluoro-2-hydroxy-2-propyl)-phenyl-carbamoyl]-2-chlorobenzcarboximidate
Ethyl N-[N-(4-(1,1,1,3,3,3-hexafluoro-2-hydroxy-2-propyl)-phenyl-carbamoyl]-2-fluorobenzcarboximidate
Ethyl N-[N-(4-(1,1,1,3,3,3-hexafluoro-2-hydroxy-2-propyl)-phenyl-carbamoyl]-2-chloro-6-fluorobenzcarboximidate
Ethyl N-[N-(4-(1,1,1,3,3,3-hexafluoro-2-hydroxy-2-propyl)-phenyl-carbamoyl]-2,6-difluorobenzcarboximidate
Ethyl N-[N-(4-(1,1,1,3,3,3-hexafluoro-2-hydroxy-2-propyl)-phenyl-carbamoyl]-2,4-dichlorobenzcarboximidate
Ethyl N-[N-(4-(1,1,1,3,3,3-hexafluoro-2-hydroxy-2-propyl)-phenyl-carbamoyl]-2-chloro-4-fluorobenzcarboximidate
Ethyl N-[N-(4-(methoxycarbonylphenyl)-carbamoyl]-2-fluorobenzcarboximidate
Ethyl N-[N-(4-(ethylphenyl)-carbamoyl]-2-fluorobenzcarboximidate
Ethyl N-[N-(4-(1,1-dimethylethyl)-phenyl)-carbamoyl]-2-fluorobenzcarboximidate
Ethyl N-[N-(4-(4-(chlorophenyl)-thiocarbamoyl]-2-fluorobenzcarboximidate
Ethyl N-[N-(4-(4-trifluoromethoxyphenyl)-carbamoyl]-2-fluorobenzthiocarboximidate
Ethyl N-[N-(4-trifluoromethoxyphenyl)-carbamoyl]-2-chlorobenzthiocarboximidate
Ethyl N-[N-(4-trifluoromethylphenyl)-carbamoyl]-2-chlorobenzthiocarboximidate
Ethyl N-[N-(2,3-dichlorophenyl)-carbamoyl]-2-fluorobenzcarboximidate
Ethyl N-[N-(2-chloro-3-methylphenyl)-carbamoyl]-2-fluorobenzcarboximidate
Ethyl N-[N-(2,4-difluorophenyl)-carbamoyl]-2-fluorobenzcarboximidate
Ethyl N-[N-(2,4-difluorophenyl)-carbamoyl]-2,4-difluorobenzcarboximidate
Ethyl N-[N-(2,4-difluorophenyl)-carbamoyl]-4-chloro-2-fluorobenzcarboximidate
Ethyl N-[N-(2,4-difluorophenyl)-carbamoyl]-5-chloro-2-fluorobenzcarboximidate
Ethyl N-[N-(2,4-difluorophenyl)-carbamoyl]-2-chloro-6-fluorobenzcarboximidate
Ethyl N-[N-(2,4-difluorophenyl)-carbamoyl]-2-chloro-4-fluorobenzcarboximidate
Ethyl N-[N-(2,4-difluorophenyl)-carbamoyl]-2-chloro-5-fluorobenzcarboximidate
Ethyl N-[N-(2,4-dichlorophenyl)-carbamoyl]-2-fluorobenzcarboximidate
Ethyl N-[N-(4-chlor-2-trifluoromethylphenyl)-carbamoyl]-2-fluorobenzcarboximidate
Ethyl N-[N-(2-chlor-4-(2-propyl-phenyl)-carbamoyl]-2-fluorobenzcarboximidate
Ethyl N-[N-(2,4-bis-(2-chloro-1,1,2-trifluoroethoxy)-phenyl)-carbamoyl]-2-fluorobenzcarboximidate
Ethyl N-[N-(2,4-bis-(2-chloro-1,1,2-trifluoroethoxy)-phenyl)-carbamoyl]-2-chlorobenzcarboximidate Ethyl N-[N-(2,4-bis-(2-chloro-1,1,2-trifluoroethoxy)-phenyl)-carbamoyl]-2,6-difluorobenzcarboximidate Ethyl N-[N-(2,4-bis-(2-chloro-1,1,2-trifluoroethoxy)-phenyl)-carbamoyl]-2-chloro-4-fluorobenzcarboximidate Ethyl N-[N-(2,4-bis-(2-chloro-1,1,2-trifluoroethoxy)-phenyl)-carbamoyl]-2-chloro-5-fluorobenzcarboximidate N-[N-(2,4-bis-(2-chloro-1,1,2-trifluoroethoxy)-phenyl)-carbamoyl]-4-chloro-2-fluorobenzcarboximidate Ethyl N-[N-(2,4-bis-(2-chloro-1,1,2-trifluoroethoxy)-phenyl)-carbamoyl]-5-chloro-2-fluorobenzcarboximidate Ethyl N-[N-(2,4-bis-(2-chloro-1,1,2-trifluoroethoxy)-phenyl)-carbamoyl]-2,4-dichlorobenzcarboximidate Ethyl N-[N-(2-chloro-5-trifluoromethylphenyl)-carbamoyl]-2-fluorobenzcarboximidate Ethyl N-[N-(2,5-difluorophenyl)-carbamoyl]-2,6-dimethoxybenzcarboximidate Ethyl N-[N-(2,5-difluorophenyl)-carbamoyl]-2,6-difluorobenzcarboximidate Ethyl N-[N-(2,6-difluorophenyl)-carbamoyl]-2,6-dimethoxybenzcarboximidate Ethyl N-[N-(2,6-dichlorophenyl)-carbamoyl]-2,6-dimethoxybenzcarboximidate Ethyl N-[N-(2,6-dibromophenyl)-carbamoyl]-2,6-dimethoxybenzcarboximidate Ethyl N-[N-(2,6-dimethoxyphenyl)-carbamoyl]-2,6-dimethoxybenzcarboximidate Ethyl N-[N-(2,6-dimethylphenyl)-carbamoyl]-2,6-difluorobenzcarboximidate Ethyl N-[N-(2,6-dimethylphenyl)-carbamoyl]-2,6-dimethoxybenzcarboximidate Ethyl N-[N-(2-ethyl-6-methylphenyl)-carbamoyl]-2,6-difluorobenzcarboximidate Ethyl N-[N-(2-ethyl-6-methylphenyl)-carbamoyl]-2,6-dimethoxybenzcarboximidate Ethyl N-[N-(3-chloro-4-fluorophenyl)-carbamoyl]-2-chlorobenzcarboximidate Ethyl N-[N-(3-chloro-4-fluorophenyl)-carbamoyl]-2-fluorobenzcarboximidate Ethyl N-[N-(4-fluoro-3-nitrophenyl)-carbamoyl]-2-fluorobenzcarboximidate Ethyl N-[N-(4-(3,5-dimethyl-1-piperidinyl)-3-fluorophenyl)-carbamoyl]-2-fluorobenzcarboximidate Ethyl N-[N-(4-(3,5-dimethyl-1-piperidinyl)-3-fluorophenyl)-carbamoyl]-2,6-difluorobenzcarboximidate Ethyl N-[N-(4-(3,5-dimethyl-1-piperidinyl)-3-fluorophenyl)-carbamoyl]-2,4-dichlorobenzcarboximidate Ethyl N-[N-(4-chloro-3-trifluoromethylphenyl)-carbamoyl]-2-fluorobenzcarboximidate Ethyl N-[N-(4-chloro-3-trifluoromethylphenyl)-carbamoyl]-2-chlorobenzcarboximidate Ethyl N-[N-(4-chloro-3-trifluoromethylphenyl)-carbamoyl]-4-chloro-2-fluorobenzcarboximidate Ethyl N-[N-(4-chloro-3-trifluoromethylphenyl)-carbamoyl]-2-chloro-6-fluorobenzcarboximidate Ethyl N-[N-(4-chloro-3-trifluoromethylphenyl)-carbamoyl]-2-chloro-4-fluorobenzcarboximidate Ethyl N-[N-(4-chloro-3-trifluoromethylphenyl)-carbamoyl]-2,4-dichlorobenzcarboximidate Ethyl N-[N-(3-chloro-4-trifluoromethoxy-phenyl)-carbamoyl]-2-fluorobenzcarboximidate Ethyl N-[N-(3-chloro-4-trifluoromethoxy-phenyl)-carbamoyl]-2,6-difluorobenzcarboximidate Ethyl N-[N-(3-chloro-4-trifluoromethoxy-phenyl)-carbamoyl]-2,4-dichlorobenzcarboximidate Ethyl N-[N-(3-chloro-4-(2-chloro-1,1,2-trifluoroethoxy)-phenyl)-carbamoyl]-2-chlorobenzbcarboximidate Ethyl N-[N-(3-chloro-4-(2-chloro-1,1,2-trifluoroethoxy)-phenyl)-carbamoyl]-2-fluorobenzcarboximidate Ethyl N-[N-(3-chloro-1,1,2-trifluoroethoxy)-phenyl)-carbamoyl]-2,6-difluorobenzcarboximidate Ethyl N-[N-(3-chloro-4-(2-chloro-1,1,2-trifluoroethoxy)-phenyl)-carbamoyl]-2-chloro-6-fluorobenzcarboximidate Ethyl N-[N-(3-chloro-4-(2-chloro-1,1,2-trifluoroethoxy)-phenyl)-carbamoyl]-2,4-dichlorobenzcarboximidate Ethyl N-[N-(3-chloro-4-(2-chloro-1,1,2-trifluoroethoxy)-phenyl)-carbamoyl]-2,6-dichlorobenzcarboximidate Ethyl N-[N-(3-chloro-4-(1,1,2,3,3,3-hexafluoro-1-propoxy)-phenyl)-carbamoyl]-2,6-difluorobenzcarboximidate Ethyl N-[N-(4-chloro-3-(2-chloro-1,1,2-trifluoroethoxy)-phenyl)-carbamoyl]-2-fluorobenzcarboximidate Ethyl N-[N-(4-chloro-3-(2-chloro-1,1,2-trifluoroethoxy)-phenyl)-carbamoyl]-2-chlorobenzcarboximidate Ethyl N-[N-(4-chloro-1,1,2-trifluoroethoxy)-phenyl)-carbamoyl]-2,6-difluorobenzcarboximidate Ethyl N-[N-(4-chloro-3-(2-chloro-1,1,2-trifluoroethoxy)-phenyl)-carbamoyl]-2-chloro-6-fluorobenzcarboximidate Ethyl N-[N-(4-chloro-3-(1,1,2,2-tetrafluoroethoxy)-phenyl)-carbamoyl]-2-fluorobenzcarboximidate Ethyl N-[N-(4-chloro-3-(1,1,2,3,3,3-hexafluoro-1-propoxy)-phenyl)-carbamoyl]-2,6-difluorobenzcarboximidate Ethyl N-[N-(3-chloro-4-trifluoromethylmercapto-phenyl)-carbamoyl]-2-chlorobenzcarboximidate Ethyl N-[N-(3-chloro-4-(2-chloro-1,1,2-trifluoroethylmercapto)-phenyl)-carbamoyl]-2,6-difluorobenzcarboximidate Ethyl N-[N-(4-chloro-3-trifluoromethylmercapto-phenyl)-carbamoyl]-2,6-difluorobenzcarboximidate Ethyl N-[N-(3-chloro-4-(3,5-dimethyl-1-piperidinyl)-phenyl)-carbamoyl]-2,6-difluorobenzcarboximidate Ethyl N-[N-(4(-bis-(2-butyl)-amino)-3-chlorophenyl)-carbamoyl]-2,6-difluorobenzcarboximidate Ethyl N-[N-(3-chloro-4-cyanophenyl)-carbamoyl]-2,6-difluorobenzcarboximidate Ethyl N-[N-(3-chloro-4-(1,1-dimethylethoxycarbonyl)-phenyl)-carbamoyl]-2-fluorobenzcarboximidate Ethyl N-[N-(3-chloro-4-(2,4-dimethyl-3-pentyloxycarbonyl)-phenyl)-carbamoyl]-2,6-difluorobenzcarboximidate Ethyl N-[N-(3-chloro-4-(3,5,5-trimethyl-1-hexyloxycarbonyl)-phenyl)-carbamoyl]-2,6-difluorobenzcarboximidate Ethyl N-[N-(3-chloro-4-methylphenyl)-carbamoyl]-2-fluorobenzcarboximidate Ethyl N-[N-(3,4-dichlorophenyl)-carbamoyl]-2-fluorobenzcarboximidate Ethyl N-[N-(3,4-dichlorophenyl)-carbamoyl]-3-fluorobenzcarboximidate Ethyl N-[N-(3,4-dichlorophenyl)-carbamoyl]-2-iodobenzcarboximidate Ethyl N-[N-(3,4-dichlorophenyl)-carbamoyl]-2-chloro-5-nitrobenzcarboximidate Ethyl N-[N-(3,4-dichlorophenyl)-carbamoyl]-2,4-dichlorobenzcarboximidate Ethyl N-[N-(3,4-dichlorophenyl)-carbamoyl]-2,5-dichlorobenzcarboximidate Ethyl N-[N-(3,4-dichlorophenyl)-carbamoyl]-pentafluorobenzcarboximidate
Ethyl N-[N-(3,4-dichlorophenyl)-carbamoyl]-3-trifluoromethoxybenzcarboximidate
Ethyl N-[N-(3,4-dichlorophenyl)-carbamoyl]-4-trifluoromethoxybenzcarboximidate
Ethyl N-[N-(3,4-dichlorophenyl)-carbamoyl]-2-methoxybenzcarboximidate
Ethyl N-[N-(3,4-dichlorophenyl)-carbamoyl]-3-nitro-5-trifluorobenzcarboximidate
Ethyl N-[N-(3,4-dichlorophenyl)-carbamoyl]-2-trifluoromethylbenzcarboximidate
Ethyl N-[N-(3,4-dichlorophenyl)-carbamoyl]-3-trifluoromethylbenzcarboximidate
Ethyl N-[N-(4-trifluoromethoxy-3-trifluoromethylphenyl)-carbamoyl]-2,6-difluorobenzcarboximidate
Ethyl N-[N-(4-(2-chloro-1,1,2-trifluoroethoxy)-3-trifluoromethylphenyl)-carbamoyl]-2,6-difluorobenzcarboximidate
Ethyl N-[N-(4-(1,1,2,2-tetrafluoroethoxy)-3-trifluoromethylphenyl)-carbamoyl]-2,6-difluorobenzcarboximidate
Ethyl N-[N-(4-(1,1,2,3,3,3-hexafluoro-1-propoxy)-3-trifluoromethylphenyl)-carbamoyl]-2,6-difluorobenzcarboximide
Ethyl N-[N-(3,4-bisdifluoromethoxyphenyl)-carbamoyl]-2,6-difluorobenzcarboximidate
Ethyl N-[N-(3,4-bistrifluoromethoxyphenyl)-carbamoyl]-2,6-difluorobenzcarboximidate
Ethyl N-[N-(2,2-difluorobenzo[1,3]dioxol-5-yl)-carbamoyl]-2-fluorobenzcarboximidate
Ethyl N-[N-(2H,3H-2,2,3-trifluorobenzo[1,4]dioxin-6-yl)-carbamoyl]-2-chlorobenzcarboximidate
Ethyl N-[N-(2H,3H-3-chloro-2,2,3-trifluorobenzo[1,4]dioxin-6-yl)-carbamoyl]-2,6-difluorobenzcarboximidate
Ethyl N-[N-(2H,3H-2,2,3,3-tetrafluorobenzo[1,4]dioxin-6-yl)-carbamoyl]-2-fluorobenzcarboximidate
Ethyl N-[N-(2H,3H-2,2,3,3-tetrafluorobenzo[1,4]dioxin-6-yl)-carbamoyl]-2-chlorobenzcarboximidate
Ethyl N-[N-(2H,3H-2,2,3,3-tetrafluorobenzo[1,4]dioxin-6-yl)-carbamoyl]-2,6-difluorobenzcarboximidate
Ethyl N-[N-(2H,3H-2,2-difluoro-3-trifluoromethylbenzo[1,4]-dioxin-6-yl)-carbamoyl]-2,6-fluorobenzcarboximidate
Ethyl N-[N-(3-methyl-4-(1-piperidinyl)-phenyl)-carbamoyl]-2,6-difluorobenzcarboximidate
Ethyl N-[N-(3,4-dimethylphenyl)-carbamoyl]-2-fluorobenzcarboximidate
Methyl N-[N-(4-chloro-3-trifluoromethylphenyl)-carbamoyl]-2-chlorobenzthiocarboximidate
Methyl N-[N-(3,4-dichlorophenyl)-carbamoyl]-2-fluorobenzthiocarboximidate
Methyl N-[N-(3,4-dichlorophenyl)-carbamoyl]-2-chlorobenzthiocarboximidate
Ethyl N-[N-(3,5-dichlorophenyl)-carbamoyl]-2-fluorobenzcarboximidate
Ethyl N-[N-(3,5-bistrifluoromethylphenyl)-carbamoyl]-2-fluorobenzcarboximidate
Ethyl N-[N-(3,5-dimethylphenyl)-carbamoyl]-2-fluorobenzcarboximide
Ethyl N-[N-(3-ethylsulfonyl-5-trifluoromethylphenyl)-carbamoyl]-2-fluorobenzcarboximidate
Ethyl N-[N-(4-(2-chloro-1,1,2-trifluoroethoxy)-2,3-dichlorophenyl)-carbamoyl]-2-fluorobenzcarboximidate
Ethyl N-[N-(4-(2-chloro-1,1,2-trifluoroethoxy)-2,3-dichlorophenyl)-carbamoyl]-2,6-difluorobenzcarboximidate
Ethyl N-[N-(4-(2-chloro-1,1,2-trifluoroethoxy)-2,3-dichlorophenyl)-carbamoyl]-2,4-dichlorobenzcarboximidate
Ethyl N-[N-(2,3-dichloro-4-(1,1,2,2-tetrafluoroethoxy)-phenyl)-carbamoyl]-2-fluorobenzcarboximidate
Ethyl N-[N-(2,3-dichloro-4-(1,1,2,2-tetrafluoroethoxy)-phenyl)-carbamoyl]-2,6-difluorobenzcarboximidate
Ethyl N-[N-(2,3-dichloro-4-(1,1,2,2-tetrafluoroethoxy)-phenyl)-carbamoyl]-2,4-dichlorobenzcarboximidate
Ethyl N-[N-(2,3-dichloro-4-(1,1,2,3,3,3-hexafluoro-1-propoxy)-phenyl)-carbamoyl]-2-fluorobenzcarboximidate
Ethyl N-[N-(2,3-dichloro-4-(1,1,2,3,3,3-hexafluoro-1-propoxy)-phenyl)-carbamoyl]-2,6-difluorobenzcarboximidate
Ethyl N-[N-(2,3-dichloro-4-(1,1,2,3,3,3-hexafluoro-1-propoxy)-phenyl)-carbamoyl]-2,4-dichlorobenzcarboximidate
Ethyl N-[N-(4-chloro-2-fluoro-5-methoxyphenyl)-carbamoyl]-2-fluorobenzcarboximidate
Ethyl N-[N-(4-chloro-2-fluoro-5-methoxyphenyl)-carbamoyl]-2,6-difluorobenzcarboximidate
Ethyl N-[N-(4-chloro-2-fluoro-5-methoxyphenyl)-carbamoyl]-2,4-dichlorobenzcarboximidate
Ethyl N-[N-(4-chloro-2-fluoro-5-methoxyphenyl)-carbamoyl]-2,6-dimethoxybenzcarboximidate
Ethyl N-[N-(4-chloro-2-fluoro-5-(2-propoxy)-phenyl)-carbamoyl]-2,6-dimethoxybenzcarboximidate
Ethyl N-[N-(5-chloro-2,4-difluorophenyl)-carbamoyl]-2-fluorobenzcarboximidate
Ethyl N-[N-(5-chloro-2,4-difluorophenyl)-carbamoyl]-2-chlorobenzcarboximidate
Ethyl N-[N-(5-chloro-2,4-difluorophenyl)-carbamoyl]-2,6-difluorobenzcarboximidate
Ethyl N-[N-(5-chloro-2,4-difluorophenyl)-carbamoyl]-2-chloro-6-fluorobenzcarboximidate
Ethyl N-[N-(5-chloro-2,4-difluorophenyl)-carbamoyl]-2,6-dichlorobenzcarboximidate
Ethyl N-[N-(5-bromo-2-chloro-4-methylphenyl)-carbamoyl]-2-fluorobenzcarboximidate
Ethyl N-[N-(2,4,5-trichlorophenyl)-carbamoyl]-2-fluorobenzcarboximidate
Ethyl N-[N-(2,4,6-trifluorophenyl)-carbamoyl]-2,6-difluorobenzcarboximidate
Ethyl N-[N-(2,4,6-trifluorophenyl)-carbamoyl]-2,6-dimethoxybenzcarboximidate
Ethyl N-[N-(2,4,6-trichlorophenyl)-carbamoyl]-2,6-dimethoxybenzcarboximidate
Ethyl N-[N-(3-chloro-4-(3-chloro-2-propen-1-yloxy)-5-trifluoromethylphenyl)-carbamoyl]-2,6-difluorobenzcarboximidate
Ethyl N-[N-(3-chloro-4-(3-bromo-2-propen-1-yloxy)-5-trifluoromethylphenyl)-carbamoyl]-2,6-difluorobenzcarboximidate
Ethyl N-[N-(3-chloro-4-(2-chloro-1,1,2-trifluoroethoxy)-5-methylphenyl)-carbamoyl]-2-trifluorobenzcarboximidate
Ethyl N-[N-(3-chloro-4-(2-chloro-1,1,2-trifluoroethoxy)-5-methylphenyl)-carbamoyl]-2-chlorobenzcarboximidate
Ethyl N-[N-(3-chloro-1,1,2-trifluoroethoxy)-5-methylphenyl)-carbamoyl]-2,6-difluorobenzcarboximidate
Ethyl N-[N-(3-chloro-4-(2-chloro-1,1,2-trifluoroethoxy)-5-methylphenyl)-carbamoyl]-2,4-dichlorobenzcarboximidate Ethyl N-[N-(3-chloro-5-methyl-4-(1,1,2,2-tetrafluoroethoxy)-phenyl)-carbamoyl]-2-fluorobenzcarboximidate
Ethyl N-[N-(3-chloro-5-methyl-4-(1,1,2,2-tetrafluoroethoxy)-phenyl)-carbamoyl]-2-chlorobenzcarboximidate
Ethyl N-[N-(3-chloro-5-methyl-4-(1,1,2,2-tetrafluoroethoxy)-phenyl)-carbamoyl]-2,6-difluorobenzcarboximidate
Ethyl N-[N-(3-chloro-5-methyl-4-(1,1,2,2-tetrafluoroethoxy)-phenyl)-carbamoyl]-2,4-dichlorobenzcarboximidate
Ethyl N-[N-(3-chloro-4-(1,1,2,3,3,3-hexafluoro-1-propoxy)-5-methylphenyl)-carbamoyl]-2-fluorobenzcarboximidate
Ethyl N-[N-(3-chloro-4-(1,1,2,3,3,3-hexafluoro-1-propoxy)-5-methylphenyl)-carbamoyl]-2-chlorobenzcarboximidate
Ethyl N-[N-(3-chloro-4-(1,1,2,3,3,3-hexafluoro-1-propoxy)-5-methylphenyl)-carbamoyl]-2,6-difluorobenzcarboximidate
Ethyl N-[N-(3-chloro-4-(1,1,2,3,3,3-hexafluoro-1-propoxy)-5-methylphenyl)-carbamoyl]-2,4-dichlorobenzcarboximidate
Ethyl N-[N-(3,5-bistrifluoromethyl-4-chlorophenyl)-carbamoyl]-2-fluorobenzcarboximidate
Ethyl N-[N-(3-bromo-4-(3-chloro-2-propen-1-yloxy)-5-trifluoromethylphenyl)-carbamoyl]-2,6-difluorobenzcarboximidate
Ethyl N-[N-(3-bromo-4-(2-propen-1-yloxy)-5-trifluoromethylphenyl)-carbamoyl]-2,6-difluorobenzcarboximidate
Ethyl N-[N-(3-bromo-5-chloro-4-(3-chloro-2-propen-1-yloxy)-phenyl)-carbamoyl]-2,6-difluorobenzcarboximidate
Ethyl N-[N-(3-bromo-5-chloro-4-(2-propen-1-yloxy)-phenyl)-carbamoyl]-2,6-difluorobenzcarboximidate
Ethyl N-[N-(3,5-dichloro-4-difluoromethoxyphenyl)-carbamoyl]-2,6-difluorobenzcarboximidate
Ethyl N-[N-(4-chlorodifluoromethoxy-3,5-dichlorophenyl)-carbamoyl]-2,6-difluorobenzcarboximidate
Ethyl N-[N-(3,5-dichloro-4-trifluoromethoxyphenyl)-carbamoyl]-2,6-difluorobenzcarboximidate
Ethyl N-[N-(4-(2-chloro-1,1,2-trifluoroethoxy)-3,5-dichlorophenyl)-carbamoyl]-2-fluorobenzcarboximidate
Ethyl N-[N-(4-(1,1,2-trifluoroethoxy)-3,5-dichlorophenyl)-carbamoyl]-2-chlorobenzcarboximidate
Ethyl N-[N-(4-(2-chloro-1,1,2-trifluoroethoxy)-3,5-dichlorophenyl)-carbamoyl]-2-chloro-6-methoxybenzcarboximidate
Ethyl N-[N-(4-(2-chloro-1,1,2-trifluoroethoxy)-3,5-dichlorophenyl)-carbamoyl]-2,4-difluorobenzcarboximidate
Ethyl N-[N-(4-(2-chloro-1,1,2-trifluoroethoxy)-3,5-dichlorophenyl)-carbamoyl]-2,6-difluorobenzcarboximidate
Ethyl N-[N-(4-(2-chloro-1,1,2-trifluoroethoxy)-3,5-dichlorophenyl)-carbamoyl]-4-chloro-2-fluorobenzcarboximidate
Ethyl N-[N-(4-(2-chloro-1,1,2-trifluoroethoxy)-3,5-dichlorophenyl)-carbamoyl]-5-chloro-2-fluorobenzcarboximidate
Ethyl N-[N-(4-(2-chloro-1,1,2-trifluoroethoxy)-3,5-dichlorophenyl)-carbamoyl]-2-chloro-6-fluorobenzcarboximidate
Ethyl N-[N-(4-(2-chloro-1,1,2-trifluoroethoxy)-3,5-dichlorophenyl)-carbamoyl]-2-chloro-4-fluorobenzcarboximidate
Ethyl N-[N-(4-(2-chloro-1,1,2-trifluoroethoxy)-3,5-dichlorophenyl)-carbamoyl]-2-chloro-5-fluorobenzcarboximidate
Ethyl N-[N-(4-(2-chloro-1,1,2-trifluoroethoxy)-3,5-dichlorophenyl)-carbamoyl]-2,4-dichlorobenzcarboximidate
Ethyl N-[N-(4-(2-chloro-1,1,2-trifluoroethoxy)-3,5-dichlorophenyl)-carbamoyl]-2,6-dichlorobenzcarboximidate
Ethyl N-[N-(4-(2-chloro-1,1,2-trifluoroethoxy)-3,5-dichlorophenyl)-carbamoyl]-3,4-dichlorobenzcarboximidate
Ethyl N-[N-(4-(2-chloro-1,1,2-trifluoroethoxy)-3,5-dichlorophenyl)-carbamoyl]-3,5-dichlorobenzcarboximidate
Ethyl N-[N-(4-(2-chloro-1,1,2-trifluoroethoxy)-3,5-dichlorophenyl)-carbamoyl]-2-difluoromethoxybenzcarboximidate
Ethyl N-[N-(4-(2-chloro-1,1,2-trifluoroethoxy)-3,5-dichlorophenyl)-carbamoyl]-2-(2,2,2-trifluoroethoxy)-benzcarboximidate
Ethyl N-[N-(4-(2-chloro-1,1,2-trifluoroethoxy)-3,5-dichlorophenyl)-carbamoyl]-2,6-bis-(2,2,2-trifluoroethoxy)-benzcarboximidate
Ethyl N-[N-(4-(2-chloro-1,1,2-trifluoroethoxy)-3,5-dichlorophenyl)-carbamoyl]-2-methoxybenzcarboximidate
Ethyl N-[N-(4-(2-chloro-1,1,2-trifluoroethoxy)-3,5-dichlorophenyl)-carbamoyl]-2,6-dimethoxybenzcarboximidate
Ethyl N-[N-(4-(2-chloro-1,1,2-trifluoroethoxy)-3,5-dichlorophenyl)-carbamoyl]-2-difluoromethylmercaptobenzcarboximidate
Ethyl N-[N-(4-(2-chloro-1,1,2-trifluoroethoxy)-3,5-dichlorophenyl)-carbamoyl]-2-difluoromethylsulfinylbenzcarboximidate
Ethyl N-[N-(4-(2-chloro-1,1,2-trifluoroethoxy)-3,5-dichlorophenyl)-carbamoyl]-2-difluoromethylsulfonylbenzcarboximidate
Ethyl N-[N-(4-(2-chloro-1,1,2-trifluoroethoxy)-3,5-dichlorophenyl)-carbamoyl]-2-trifluoromethylbenzcarboximidate
Ethyl N-[N-(4-(2-chloro-1,1,2-trifluoroethoxy)-3,5-dichlorophenyl)-carbamoyl]-2-methylbenzcarboximidate
Ethyl N-[N-(4-(2-bromo-1,1,2-trifluoroethoxy)-3,5-dichlorophenyl)-carbamoyl]-2-fluorobenzcarboximidate
Ethyl N-[N-(4-(2-bromo-1,1,2-trifluoroethoxy)-3,5-dichlorophenyl)-carbamoyl]-2-chlorobenzcarboximidate
Ethyl N-[N-(4-(2-bromo-1,1,2-trifluoroethoxy)-3,5-dichlorophenyl)-carbamoyl]-2,6-difluorobenzcarboximidate
Ethyl N-[N-(4-(2-bromo-1,1,2-trifluoroethoxy)-3,5-dichlorophenyl)-carbamoyl]-2-chloro-6-fluorobenzcarboximidate
Ethyl N-[N-(4-(2-bromo-1,1,2-trifluoroethoxy)-3,5-dichlorophenyl)-carbamoyl]-2,6-dichlorobenzcarboximidate
Ethyl N-[N-(4-(2-bromo-1,1,2-trifluoroethoxy)-3,5-dichlorophenyl)-carbamoyl]-2,4-dichlorobenzcarboximidate
Benzyl N-[N-(3,5-dichloro-4-(1,1,2,2-tetrafluoroethoxy)-phenyl)-carbamoyl]-2-fluorobenzcarboximidate
4-Chlorobenzyl N-[N-(3,5-dichloro-4-(1,1,2,2-tetrafluoroethoxy)-phenyl)-carbamoyl]-2-fluorobenzcarboximidate Methyl N-[N-(3,5-dichloro-4-(1,1,2,2-tetrafluoroethoxy)-phenyl)-carbamoyl]-2-fluorobenzcarboximidate
Ethyl N-[N-(3,5-dichloro-4-(1,1,2,2-tetrafluoroethoxy)-phenyl)-carbamoyl]-2-fluorobenzcarboximidate
2,2,2-Trifluoroethyl N-[N-(3,5-dichloro-4-(1,1,2,2-tetrafluoroethoxy)phenyl)-carbamoyl]-2-fluorobenzcarboximidate
2,2,2-Trichloroethyl N-[N-(3,5-dichloro-4-(1,1,2,2-tetrafluoroethoxy)phenyl)-carbamoyl]-2-fluorobenzcarboximidate
Ethyl N-[N-(3,5-dichloro-4-(1,1,2,2-tetrafluoroethoxy)-phenyl)-carbamoyl]-2-fluoro-5-nitrobenzcarboximidate
Ethyl N-[N-(3,5-dichloro-4-(1,1,2,2-tetrafluoroethoxy)-phenyl)-carbamoyl]-2-chlorobenzcarboximidate
Ethyl N-[N-(3,5-dichloro-4-(1,1,2,2-tetrafluoroethoxy)-phenyl)-carbamoyl]-4-chlorobenzcarboximidate
Ethyl N-[N-(3,5-dichloro-4-(1,1,2,2-tetrafluoroethoxy)-phenyl)-carbamoyl]-2,4-difluorobenzcarboximidate
Ethyl N-[N-(3,5-dichloro-4-(1,1,2,2-tetrafluoroethoxy)-phenyl)-carbamoyl]-2,6-difluorobenzcarboximidate
Ethyl N-[N-(3,5-dichloro-4-(1,1,2,2-tetrafluoroethoxy)-phenyl)-carbamoyl]-4-chloro-2-fluorobenzcarboximidate
Ethyl N-[N-(3,5-dichloro-4-(1,1,2,2-tetrafluoroethoxy)-phenyl)-carbamoyl]-5-chloro-2-fluorobenzcarboximidate
Ethyl N-[N-(3,5-dichloro-4-(1,1,2,2-tetrafluoroethoxy)-phenyl)-carbamoyl]-2-chloro-6-fluorobenzcarboximidate
Ethyl-N-[N-(3,5-dichloro-4-(1,1,2,2-tetrafluoroethoxy)-phenyl)-carbamoyl]-2-chloro-4-fluorobenzcarboximidate
Ethyl-N-[N-(3,5-dichloro-4-(1,1,2,2-tetrafluoroethoxy)-phenyl)-carbamoyl]-2-chloro-5-fluorobenzcarboximidate
Ethyl N-[N-(3,5-dichloro-4-(1,1,2,2-tetrafluoroethoxy)-phenyl)-carbamoyl]-2-chloro-6-methoxybenzcarboximidate
Ethyl N-[N-(3,5-dichloro-4-(1,1,2,2-tetrafluoroethoxy)-phenyl)-carbamoyl]-2,4-dichlorobenzcarboximidate
Ethyl-N-[N-(3,5-dichloro-4-(1,1,2,2-tetrafluoroethoxy)-phenyl)-carbamoyl]-2,6-dichlorobenzcarboximidate
Ethyl N-[N-(3,5-dichloro-4-(1,1,2,2-tetrafluoroethoxy)-phenyl)-carbamoyl]-3,4-dichlorobenzcarboximidate
Ethyl N-[N-(3,5-dichloro-4-(1,1,2,2-tetrafluoroethoxy)-phenyl)-carbamoyl]-3,5-dichlorobenzcarboximidate
Ethyl N-[N-(3,5-dichloro-4-(1,1,2,2-tetrafluoroethoxy)-phenyl)-carbamoyl]-2-difluoromethoxybenzcarboximidate
Ethyl N-[N-(3,5-dichloro-4-(1,1,2,2-tetrafluoroethoxy)-phenyl)-carbamoyl]-2-(2,2,2-trifluoroethoxy)-benzcarboximidate
Ethyl N-[N-(3,5-dichloro-4-(1,1,2,2-tetrafluoroethoxy)-phenyl)-carbamoyl]-2,6-bis-(2,2,2-trifluoroethoxy)-benzcarboximidate
Ethyl N-[N-(3,5-dichloro-4-(1,1,2,2-tetrafluoroethoxy)-phenyl)-carbamoyl]-2-methoxybenzcarboximidate
Ethyl N-[N-(3,5-dichloro-4-(1,1,2,2-tetrafluoroethoxy)-phenyl)-carbamoyl]-2,6-dimethoxybenzcarboximidate
Ethyl N-[N-(3,5-dichloro-4-(1,1,2,2-tetrafluoroethoxy)-phenyl)-carbamoyl]-2-methylsulfonyloxybenzcarboximidate
Ethyl N-[N-(3,5-dichloro-4-(1,1,2,2-tetrafluoroethoxy)-phenyl)-carbamoyl]-2-difluoromethylmercaptobenzcarboximidate
Ethyl N-[N-(3,5-dichloro-4-(1,1,2,2-tetrafluoroethoxy)-phenyl)-carbamoyl]-2-difluoromethylsulfinylbenzcarboximidate
Ethyl N-[N-(3,5-dichloro-4-(1,1,2,2-tetrafluoroethoxy)-phenyl)-carbamoyl]-2-difluoromethylsulfonylbenzcarboximidate
Ethyl N-[N-(3,5-dichloro-4-(1,1,2,2-tetrafluoroethoxy)-phenyl)-carbamoyl]-2-methylbenzcarboximidate
Ethyl N-[N-(3,5-dichloro-4-(1,1,2,2-tetrafluoroethoxy)-phenyl)-carbamoyl]-2-trifluoromethylbenzcarboximidate
1-Propyl N-[N-(3,5-dichloro-4-(1,1,2,2-tetrafluoroethoxy)-phenyl)-carbamoyl]-2-fluorobenzcarboximidate
Allyl N-[N-(3,5-dichloro-4-(1,1,2,2-tetrafluoroethoxy)-phenyl)-carbamoyl]-2-fluorobenzcarboximidate
Propargyl N-[N-(3,5-dichloro-4-(1,1,2,2-tetrafluoroethoxy)-phenyl)-carbamoyl]-2-fluorobenzcarboximidate
1-Butyl N-[N-(3,5-dichloro-4-(1,1,2,2-tetrafluoroethoxy)-phenyl)-carbamoyl]-2-fluorobenzcarboximidate
1-Hexyl N-[N-(3,5-dichloro-4-(1,1,2,2-tetrafluoroethoxy)-phenyl)-carbamoyl]-2-fluorobenzcarboximidate
Cyclohexyl N-[N-(3,5-dichloro-4-(1,1,2,2-tetrafluoroethoxy)phenyl)-carbamoyl]-2-fluorobenzcarboximidate
Ethyl N-[N-(4-(2,2-dibromo-1,1-difluoroethoxy)-3,5-dichlorophenyl]-carbamoyl]-2,6-difluorocarboximidate
Ethyl N-[N-(4-(2,2-dichloro-1,1-difluoroethoxy)-3,5-dichlorophenyl]-carbamoyl]-2,6-difluorobenzcarboximidate
Ethyl N-[N-(4-(2-chloro-1,1-difluoroethoxy)-3,5-dichlorophenyl]-carbamoyl]-2,6-difluorobenzcarboximidate
Cyclohexyl N-[N-(3,5-dichloro-4-pentafluoroethoxyphenyl)-carbamoyl]-2,6-difluorobenzcarboximidate
Ethyl N-[N-(3,5-dichloro-4-(1,2-dichloro-1,2-difluoroethoxy)-phenyl)-carbamoyl]-2,6-difluorobenzcarboximidate
Ethyl N-[N-(3,5-dichloro-4-(1,1,2,3,3,3-hexafluoro-1-propoxy)-phenyl)-carbamoyl]-2-fluorobenzcarboximidate
Ethyl N-[N-(3,5-dichloro-4-(1,1,2,3,3,3-hexafluoro-1-propoxy)-phenyl)-carbamoyl]-2-chlorobenzcarboximidate
Ethyl N-[N-(3,5-dichloro-4-(1,1,2,3,3,3-hexafluoro-1-propoxy)-phenyl)-carbamoyl]-2-chloro-6-methoxybenzcarboximidate
Ethyl N-[N-(3,5-dichloro-4-(1,1,2,3,3,3-hexafluoro-1-propoxy)-phenyl)-carbamoyl]-2,4-difluorobenzcarboximidate
Ethyl N-[N-(3,5-dichloro-(1,1,2,3,3,3-hexafluoro-1-propoxy)-phenyl)-carbamoyl]-2,6-difluorobenzcarboximidate
Ethyl N-[N-(3,5-dichloro-4-(1,1,2,3,3,3-hexafluoro-1-propoxy)-phenyl)-carbamoyl]-4-chloro-2-fluorobenzcarboximidate
Ethyl N-[N-(3,5-dichloro-4-(1,1,2,3,3,3-hexafluoro-1-propoxy)-phenyl)-carbamoyl]-5-chloro-2-fluorobenzcarboximidate
Ethyl N-[N-(3,5-dichloro-4-(1,1,2,3,3,3-hexafluoro-1-propoxy)-phenyl)-carbamoyl]-2-chloro-6-fluorobenzcarboximidate
Ethyl N-[N-(3,5-dichloro-4-(1,1,2,3,3,3-hexafluoro-1-propoxy)-phenyl)-carbamoyl]-2-chloro-4-fluorobenzcarboximidate Ethyl N-[N-(3,5-dichloro-4-(1,1,2,3,3,3-hexafluoro-1-propoxy)-phenyl)-carbamoyl]-2-chloro-5-fluorobenzcarboximidate Ethyl N-[N-(3,5-dichloro-4-(1,1,2,3,3,3-hexafluoro-1-propoxy)-phenyl)-carbamoyl]-2,4-dichlorobenzcarboximidate Ethyl N-[N-(3,5-dichloro-4-(1,1,2,3,3,3-hexafluoro-1-propoxy)-phenyl)-carbamoyl]-2,6-dichlorobenzcarboximidate Ethyl N-[N-(3,5-dichloro-4-(1,1,2,3,3,3-hexafluoro-1-propoxy)-phenyl)-carbamoyl]-3,4-dichlorobenzcarboximidate Ethyl N-[N-(3,5-dichloro-4-(1,1,2,3,3,3-hexafluoro-1-propoxy)-phenyl)-carbamoyl]-3,5-dichlorobenzcarboximidate Ethyl N-[N-(3,5-dichloro-4-(1,1,2,3,3,3-hexafluoro-1-propoxy)-phenyl)-carbamoyl]-2-difluoromethoxybenzcarboximidate Ethyl N-[N-(3,5-dichloro-4-(1,1,2,3,3,3-hexafluoro-1-propoxy)-phenyl)-carbamoyl]-2-(2,2,2-trifluoroethoxy)-benzcarboximidate Ethyl N-[N-(3,5-dichloro-4-(1,1,2,3,3,3-hexafluoro-1-propoxy)-phenyl)-carbamoyl]-2,6-bis-(2,2,2-trifluoroethoxy)-benzcarboximidate Ethyl N-[N-(3,5-dichloro-4-(1,1,2,3,3,3-hexafluoro-1-propoxy)-phenyl)-carbamoyl]-2-methoxybenzcarboximidate Ethyl N-[N-(3,5-dichloro-4-(1,1,2,3,3,3-hexafluoro-1-propoxy)-phenyl)-carbamoyl]-2,6-dimethoxybenzcarboximidate Ethyl N-[N-(3,5-dichloro-4-(1,1,2,3,3,3-hexafluoro-1-propoxy)-phenyl)-carbamoyl]-2-difluoromethylmercaptobenzcarboximidate Ethyl N-[N-(3,5-dichloro-4-(1,1,2,3,3,3-hexafluoro-1-propoxy)-phenyl)-carbamoyl]-2-difluoromethylsulfinylbenzcarboximidate Ethyl N-[N-(3,5-dichloro-4-(1,1,2,3,3,3-hexafluoro-1-propoxy)-phenyl)-carbamoyl]-2-difluoromethylsulfonylbenzcarboximidate Ethyl N-[N-(3,5-dichloro-4-(1,1,2,3,3,3-hexafluoro-1-propoxy)-phenyl)-carbamoyl]-2-trifluoromethylbenzcarboximidate Ethyl N-[N-(3,5-dichloro-4-(1,1,2,3,3,3-hexafluoro-1-propoxy)-phenyl)-carbamoyl]-2-methylbenzcarboximidate Ethyl N-[N-(3,5-dichloro-4-(1,1,2,3,3,4,4,4-octafluoro-1-butoxy)-phenyl)-carbamoyl]-2,6-difluorobenzcarboximidate Ethyl N-[N-(3,5-dichloro-4-(2,2,2-trifluoroethoxy)-phenyl)-carbamoyl]-2-fluorobenzcarboximidate Ethyl N-[N-(3,5-dichloro-4-(2,2,2-trifluoroethoxy)-phenyl)-carbamoyl]-2-chlorobenzcarboximidate Ethyl N-[N-(3,5-dichloro-4-(2,2,2-trifluoroethoxy)-phenyl)-carbamoyl]-2,6-difluorobenzcarboximidate Ethyl N-[N-(3,5-dichloro-4-(2,2,2-trifluoroethoxy)-phenyl)-carbamoyl]-2,4-dichlorobenzcarboximidate Ethyl N-[N-(3,5-dichloro-4-(2,2,3,3-tetrafluoro-1-propoxy)-phenyl)-carbamoyl]-2-fluorobenzcarboximidate Ethyl N-[N-(3,5-dichloro-4-(2,2,3,3-tetrafluoro-1-propoxy)-phenyl)-carbamoyl]-2-chlorobenzcarboximidate Ethyl N-[N-(3,5-dichloro-4-(2,2,3,3-tetrafluoro-1-propoxy)-phenyl)-carbamoyl]-2,6-difluorobenzcarboximidate Ethyl N-[N-(3,5-dichloro-4-(2,2,3,3-tetrafluoro-1-propoxy)-phenyl)-carbamoyl]-2,4-dichlorobenzcarboximidate Ethyl N-[N-(3,5-dichloro-4-(2,2,3,4,4,4-hexafluoro-1-butoxy)-phenyl)-carbamoyl]-2,6-difluorobenzcarboximidate Ethyl N-[N-(3,5-dichloro-4-(2,2,3,3,4,4,4-heptafluoro-1-butoxy)-phenyl)-carbamoyl]-2,6-difluorobenzcarboximidate Ethyl N-[N-(3,5-dichloro-4-(2,2,3,4,4,5,5,5-octafluoro-1-pentoxy)-phenyl)-carbamoyl]-2,6-difluorobenzcarboximidate Ethyl N-[N-(4-(4-chlorobenzyloxy)-3,5-dichlorophenyl)-carbamoyl]-2-fluorobenzcarboximidate Ethyl N-[N-(4-(4-chlorobenzyloxy)-3,5-dichlorophenyl)-carbamoyl]-2,6-difluorobenzcarboximidate Ethyl N-[N-(3,5-dichloro-4-(4-trifluoromethylbenzyloxy)-phenyl)-carbamoyl]-2-fluorobenzcarboximidate Ethyl N-[N-(3,5-dichloro-4-(4-trifluoromethylbenzyloxy)-phenyl)-carbamoyl]-2,6-difluorobenzcarboximidate Ethyl N-[N-(4-(3-chloro-4-trifluoromethylbenzyloxy)-3,5-dichlorophenyl)-carbamoyl]-2-fluorobenzcarboximidate Ethyl N-[N-(4-(3-chloro-4-trifluoromethylbenzyloxy)-3,5-dichlorophenyl)-carbamoyl]-2,6-difluorobenzcarboximidate Ethyl N-[N-(4-(2-chloro-4-trifluoromethylbenzyloxy)-3,5-dichlorophenyl)-carbamoyl]-2-fluorobenzcarboximidate Ethyl N-[N-(4-(2-chloro-4-trifluoromethylbenzyloxy)-3,5-dichlorophenyl)-carbamoyl]-2,6-difluorobenzcarboximidate Ethyl N-[N-(3,5-dichloro-4-(4-nitrobenzyloxy)-phenyl)-carbamoyl]-2-fluorobenzcarboximidate Ethyl N-[N-(3,5-dichloro-4-(4-nitrobenzyloxy)-phenyl)-carbamoyl]-2,6-difluorobenzcarboximidate Ethyl N-[N-(4-(2,4-dichlorobenzyloxy)-3,5-dichlorophenyl)-carbamoyl]-2-fluorobenzcarboximidate Ethyl N-[N-(4-(2,4-dichlorobenzyloxy)-3,5-dichlorophenyl)-carbamoyl]-2,6-difluorobenzcarboximidate Ethyl N-[N-(4-(4-cyanobenzyloxy)-3,5-dichlorophenyl)-carbamoyl]-2-fluorobenzcarboximidate Ethyl N-[N-(4-(4-cyanobenzyloxy)-3,5-dichlorophenyl)-carbamoyl]-2,6-difluorobenzcarboximidate Ethyl N-[N-(3,5-dichloro-4-(4-trifluoromethoxybenzyloxy)-phenyl)-carbamoyl]-2-fluorobenzcarboximidate Ethyl N-[N-(3,5-dichloro-4-(4-trifluoromethoxybenzyloxy)-phenyl)-carbamoyl]-2,6-difluorobenzcarboximidate Ethyl N-[N-(4-benzyloxy-3,5-dichlorophenyl)-carbamoyl]-2,6-difluorobenzcarboximidate Ethyl N-[N-(3,5-dichloro-4-(4-fluorobenzyloxy)-phenyl)-carbamoyl]-2,6-difluorobenzcarboximidate Ethyl N-[N-(3,5-dichloro-4-pentafluorobenzyloxy-phenyl)-carbamoyl]-2,6-difluorobenzcarboximidate Ethyl N-[N-(3,5-dichloro-4-(1,2-dichloroethenyloxy)-phenyl)-carbamoyl]-2-fluorobenzcarboximidate Ethyl N-[N-(3,5-dichloro-4-(1,2-dichloroethenyloxy)-phenyl)-carbamoyl]-2-chlorobenzcarboximidate Ethyl N-[N-(3,5-dichloro-4-(1,2-dichloroethenyloxy)-phenyl)-carbamoyl]-2,6-difluorobenzcarboximidate Ethyl N-[N-(3,5-dichloro-4-(1,2-dichloroethenyloxy)-phenyl)-carbamoyl]-4-chloro-2-fluorobenzcarboximidate Ethyl N-[N-(3,5-dichloro-4-(1,2-dichloroethenyloxy)-phenyl)-carbamoyl]-2-chloro-6-fluorobenzcarboximidate Ethyl N-[N-(3,5-dichloro-4-(1,2-dichloroethenyloxy)-phenyl)-carbamoyl]-2-chloro-4-fluorobenzcarboximidate Ethyl N-[N-(3,5-dichloro-4-(1,2-dichloroethenyloxy)-phenyl)carbamoyl]-5-chloro-2-fluorobenzcarboximidate Ethyl N-[N-(3,5-dichloro-4-(1,2-dichloroethenyloxy)-phenyl)-carbamoyl]-2,4-dichlorobenzcarboximidate Ethyl N-[N-(4-(3-chloro-2-propen-1-yloxy)-3,5-dichlorophenyl)-carbamoyl]-2,6-difluorobenzcarboximidate Ethyl N-[N-(4-(3-bromo-2-propen-1-yloxy)-3,5-dichlorophenyl)-carbamoyl]-2,6-difluorobenzcarboximidate Ethyl N-[N-(4-allyloxy-3,5-dichlorophenyl)-carbamoyl]-2,6-difluorobenzcarboximidate Ethyl N-[N-(3,5-dichloro-4-difluoromethylmercapto-phenyl)-carbamoyl]-2-fluorobenzcarboximidate Ethyl N-[N-(3,5-dichloro-4-difluoromethylmercapto-phenyl)-carbamoyl]-2-chlorobenzcarboximidate Ethyl N-[N-(3,5-dichloro-4-difluoromethylmercapto-phenyl)-carbamoyl]-2,6-difluorobenzcarboximidate Ethyl N-[N-(3,5-dichloro-4-difluoromethylmercapto-phenyl)-carbamoyl]-4-chloro-2-fluorobenzcarboximidate Ethyl N-[N-(3,5-dichloro-4-difluoromethylmercapto-phenyl)-carbamoyl]-2-chloro-4-fluorobenzcarboximidate Ethyl N-[N-(3,5-dichloro-4-difluoromethylmercapto-phenyl)-carbamoyl]-2,4-dichlorobenzcarboximidate Ethyl N-[N-(4-chlorodifluoromethylmercapto-3,5-dichlorophenyl)-carbamoyl]-2-fluorobenzcarboximidate Ethyl N-[N-(4-chlorodifluoromethylmercapto-3,5-dichlorophenyl)-carbamoyl]-2-chlorobenzcarboximidate Ethyl N-[N-(4-chlorodifluoromethylmercapto-3,5-dichlorophenyl)-carbamoyl]-2,6-difluorobenzcarboximidate Ethyl N-[N-(3,5-dichloro-4-trifluoromethylmercapto-phenyl)-carbamoyl]-2-fluorobenzcarboximidate Ethyl N-[N-(3,5-dichloro-4-trifluoromethylmercapto-phenyl)-carbamoyl]-2-chlorobenzcarboximidate Ethyl N-[N-(3,5-dichloro-4-trifluoromethylmercapto-phenyl)-carbamoyl]-2,6-difluorobenzcarboximidate Ethyl N-[N-(4-(2-chloro-1,1,2-trifluoromethylmercapto)-3,5-dichlorophenyl)-carbamoyl]-2-fluorobenzcarboximidate Ethyl N-[N-(4-(2-chloro-1,1,2-trifluoromethylmercapto)-3,5-dichlorophenyl)-carbamoyl]-2-chlorobenzcarboximidate Ethyl N-[N-(4-(2-chloro-1,1,2-trifluoromethylmercapto)-3,5-dichlorophenyl)-carbamoyl]-2,6-difluorobenzcarboximidate Ethyl N-[N-(4-(2-chloro-1,1,2-trifluoromethylmercapto)-3,5-dichlorophenyl)-carbamoyl]-2,4-dichlorobenzcarboximidate Ethyl N-[N-(3,5-dichloro-4-(1,1,2,2-tetrafluoroethylmercapto)-phenyl)-carbamoyl]-2-fluorobenzcarboximidate Ethyl N-[N-(3,5-dichloro-4-(1,1,2,2-tetrafluoroethylmercapto)-phenyl)-carbamoyl]-2-chlorobenzcarboximidate Ethyl N-[N-(3,5-dichloro-4-(1,1,2,2-tetrafluoroethylmercapto)-phenyl)-carbamoyl]-2,6-difluorobenzcarboximidate Ethyl N-[N-(3,5-dichloro-4-(1,1,2,2-tetrafluoroethylmercapto)-phenyl)-carbamoyl]-2,4-dichlorobenzcarboximidate Ethyl N-[N-(3,5-dichloro-4-(1,1,2,3,3,3,-hexafluoro-1-propylmercapto)-phenyl)-carbamoyl]-2-fluorobenzcarboximidate Ethyl N-[N-(3,5-dichloro-4-(1,1,2,3,3,3-hexafluoro-1-propylmercapto)-phenyl)-carbamoyl]-2-chlorobenzcarboximidate Ethyl N-[N-(3,5-dichloro-4-(1,1,2,3,3,3-hexafluoro-1-propylmercapto)-phenyl)-carbamoyl]-2,6-difluorobenzcarboximidate Ethyl N-[N-(3,5-dichloro-4-(1,1,2,3,3,3-hexafluoro-1-propylmercapto)-phenyl)-carbamoyl]-2,4-dichlorobenzcarboximidate Ethyl N-[N-(4-(3-bromo-2-propen-1-ylmercapto)-3,5-dichlorophenyl)-carbamoyl]-2,6-difluorobenzcarboximidate Ethyl N-[N-(4-(3-chloro-2-propen-1-ylmercapto)-3,5-dichlorophenyl)-carbamoyl]-2,6-difluorobenzcarboximidate Ethyl N-[N-(3,5-dichloro-4-(1-pyrrolidinyl)-phenyl)-carbamoyl]-2-fluorobenzcarboximidate Ethyl N-[N-(3,5-dichloro-4-(1-pyrrolidinyl)-phenyl)-carbamoyl]-2-chlorobenzcarboximidate Ethyl N-[N-(3,5-dichloro-4-(1-pyrrolidinyl)-phenyl)-carbamoyl]-2,6-difluorobenzcarboximidate Ethyl N-[N-(3,5-dichloro-4-(1-pyrrolidinyl)-phenyl)-carbamoyl]-2,4-dichlorobenzcarboximidate Ethyl N-[N-(3,5-dichloro-4-(4-morpholinyl)-phenyl)-carbamoyl]-2,6-difluorobenzcarboximidate Ethyl N-[N-(3,5-dichloro-4-(4-methyl-1-piperazinyl)-phenyl)-carbamoyl]-2,6-difluorobenzcarboximidate Ethyl N-[N-(3,5-dibromo-4-(1-pyrrolidinyl)-pyrrolidinyl)-phenyl)-carbamoyl]-2,6-difluorobenzcarboximidate Ethyl N-[N-(3,5-dibromo-4-(1-piperidinyl)-phenyl)-carbamoyl]-2,6-difluorobenzcarboximidate Ethyl N-[N-(4-(N-allyl,N-methylamino)-3,5-dichlorophenyl)-carbamoyl]-2,6-difluorobenzcarboximidate Ethyl N-[N-(4-(4-allyl,N-(1-butyl)-amino)-3,5-dichlorophenyl)-carbamoyl]-2,6-difluorobenzcarboximidate Ethyl N-[N-(3,5-dichloro-4-(N,N-dimethylamino)-phenyl)-carbamoyl]-2,6-difluorobenzcarboximidate Ethyl N-[N-(4-(N-(3-chloroallyl,N-methylamino)-3,5-dichlorophenyl)-carbamoyl]-2,6-difluorobenzcarboximidate Ethyl N-[N-(4-(N-(3-bromoallyl,N-methylamino)-3,5-dichlorophenyl)-carbamoyl]-2,6-difluorobenzcarboximidate Ethyl N-[N-(4-(N-(3-bromoallyl,N-methylamino)-3,5-dichlorophenyl)-carbamoyl]-2,6-difluorobenzcarboximidate Ethyl N-[N-(4-(N-(3-bromoallyl,N-(1-butyl)-amino)-3,5-dichlorophenyl)-carbamoyl]-2,6-difluorobenzcarboximidate Ethyl N-[N-(4-(N-(3-chloroallyl),N-(butyl)-amino)-3,5-dichlorophenyl)-carbamoyl]-2,6-difluorobenzcarboximidate Ethyl N-[N-(3,5-dichloro-4-(N-methyl,N-propargylamino)-phenyl)-carbamoyl]-2,6-difluorobenzcarboximidate Ethyl N-[N-(3,5-dichloro-4-(N-ethyl,N-propargylamino)-phenyl)-carbamoyl]-2,6-difluorobenzcarboximidate Ethyl N-[N-(3,5-dichloro-4-(N,N-dipropargyl)-phenyl)-carbamoyl]-2,6-difluorobenzcarboximidate Ethyl N-[N-(3,5-dichloro-4-(N-methyl,N-(1-propyl)-amino)-phenyl)-carbamoyl]-2,6-chlorobenzcarboximidate Ethyl N-[N-(3,5-dichloro-4-(N-methyl,N-(1-propyl)-amino)-phenyl)-carbamoyl]-2,6-difluorobenzcarboximidate Ethyl N-[N-(4-cyano-3,5-dichlorophenyl)-carbamoyl]-2-fluorobenzcarboximidate Ethyl N-[N-(4-cyano-3,5-dichlorophenyl)-carbamoyl]-2-chlorobenzcarboximidate Ethyl N-[N-(4-cyano-3,5-dichlorophenyl)-carbamoyl]-2,6-difluorobenzcarboximidate Ethyl N-[N-(4-cyano-3,5-dichlorophenyl)-carbamoyl]-2,4-dichlorobenzcarboximidate Ethyl N-[N-(3,5-dichloro-4-(1,1-dimethylethoxycarbonyl)-phenyl)-carbamoyl]-2,6-difluorobenzcarboximidate Ethyl N-[N-(3,5-dichloro-4-(2,4-dimethyl-3-pentyloxycarbonyl)-phenyl)-carbamoyl]-2,6-difluorobenzcarboximidate Ethyl N-[N-(3,5-dichloro-4-(1-heptyloxycarbonyl)-phenyl)-carbamoyl]-2,6-difluorobenzcarboximidate Ethyl N-[N-(3,5-dichloro-4-(3,5,5-trimethyl-1-hexyloxycarbonyl)-phenyl)-carbamoyl]-2,6-difluorobenzcarboximidate Ethyl N-[N-(4-(2-chloro-1,1,2-trifluoroethoxy-3,5-dibromophenyl)-carbamoyl]-2,6-difluorobenzcarboximidate Ethyl N-[N-(3,5-dibromo-4-(1,1,2,2-tetrafluoroethoxy)-phenyl)-carbamoyl]-2,6-difluorobenzcarboximidate Ethyl N-[N-(3,5-dibromo-4-(1,1,2,3,3,3-hexafluoro-1-propoxy)-phenyl)-carbamoyl]-2,6-difluorobenzcarboximidate Ethyl N-[N-(3,5-bistrifluoromethyl-4-difluoromethoxyphenyl)-carbamoyl]-2,6-difluorobenzcarboximidate Ethyl N-[N-(3,5-bistrifluoromethyl-4-(2-chloro-1,1,2-trifluoroethoxy)-phenyl)-carbamoyl]-2,6-fluorobenzcarboximidate Ethyl N-[N-3,5-bistrifluoromethyl-4-(1,1,2,2-tetrafluoroethoxy)-phenyl)-carbamoyl]-2,6-difluorobenzcarboximidate Ethyl N-[N-(3,5-bistrifluoromethyl-4-(1,1,2,3,3,3-hexafluoro-1-propoxy)-phenyl)-carbamoyl]-2,6-difluorobenzcarboximidate Ethyl N-[N-(4-difluoromethoxy-3,5-dimethylphenyl)-carbamoyl]-2-fluorobenzcarboximidate Ethyl N-[N-(4-chlorodifluoromethoxy-3,5-dimethylphenyl)-carbamoyl]-2-chlorobenzcarboximidate Ethyl N-[N-(3,5-dimethyl-4-trifluoromethoxyphenyl)-carbamoyl]-2,6-difluorobenzcarboximidate Ethyl N-[N-(4-(2-chloro-1,1,2-trifluoroethoxy)-3,5-dimethylphenyl)-carbamoyl]-2-fluorobenzcarboximidate Ethyl N-[N-(4-(2-chloro-1,1,2-trifluoroethoxy)-3,5-dimethylphenyl)-carbamoyl]-2-chlorobenzcarboximidate Ethyl N-[N-(4-(2-chloro-1,1,2-trifluoroethoxy)-3,5-dimethylphenyl)-carbamoyl]-2,6-difluorobenzcarboximidate Ethyl N-[N-(4-(2-chloro-1,1,2-trifluoroethoxy)-3,5-dimethylphenyl)-carbamoyl]-2,4-dichlorobenzcarboximidate Ethyl N-[N-(3,5-dimethyl-4-(1,1,2,2-tetrafluoroethoxy)-phenyl)-carbamoyl]-2-fluorobenzcarboximidate Ethyl N-[N-(3,5-dimethyl-4-(1,1,2,2-tetrafluoroethoxy)-phenyl)-carbamoyl]-2-chlorobenzcarboximidate Ethyl N-[N-(3,5-dimethyl-4-(1,1,2,2-tetrafluoroethoxy)-phenyl)-carbamoyl]-2,6-difluorobenzcarboximidate Ethyl N-[N-(3,5-dimethyl-4-(1,1,2,2-tetrafluoroethoxy)-phenyl)-carbamoyl]-2,4-dichlorobenzcarboximidate Ethyl N-[N-(3,5-dimethyl-4-(1,1,2,2-tetrafluoroethoxy)-phenyl)-carbamoyl]-2-chloro-B 4-fluorobenzcarboximidate Ethyl N-[N-(3,5-dimethyl-4-(1,1,2,3,3,3-hexafluoro-1-propoxy)-phenyl)-carbamoyl]-2-fluorobenzcarboximidate Ethyl N-[N-(3,5-dimethyl-4-(1,1,2,3,3,3-hexafluoro-1-propoxy)-phenyl)-carbamoyl]-2-chlorobenzcarboximidate Ethyl N-[N-(3,5-dimethyl-4-(1,1,2,3,3,3-hexafluoro-1-propoxy)-phenyl)-carbamoyl]-2,6-difluorobenzcarboximidate Ethyl N-[N-(3,5-dimethyl-4-(1,1,2,3,3,3-hexafluoro-1-propoxy)-phenyl)-carbamoyl]-2,4-dichlorobenzcarboximidate Ethyl N-[N-(4-1,2-dichloroethenyloxy)-3,5-dimethylphenyl)-carbamoyl]-2,6-difluorobenzcarboximidate Ethyl N-[N-(3-chloro-4-(1,2-dichloroethenyloxy)-5-methylphenyl)-carbamoyl]-2,6-difluorobenzcarboximidate Ethyl N-[N-(3,5-dichloro-4-(1,1,2,2-tetrafluoroethoxy)-phenyl)-thiocarbamoyl]-2,6-difluorobenzcarboximidate Ethyl N-[N-(4-(2-chloro-1,1,2-trifluoroethoxy)-3,5-dichlorophenyl)-thiocarbamoyl]-2,6-difluorobenzcarboximidate Ethyl N-[N-(3,5-dichloro-4-(1,1,2,3,3,3-hexafluoro-1-propoxy)-phenyl)-thiocarbamoyl]-2,6-difluorobenzcarboximidate Ethyl N-[N-(3,5-dichloro-4-(1,1,2,2-tetrafluoroethoxy)-phenyl)-carbamoyl]-2,6-difluorobenzthiocarboximidate Ethyl N-[N-(4-(2-chloro-1,1,2-trifluoroethoxy)-3,5-dichlorophenyl)-carbamoyl]-2,6-difluorobenzthiocarboximidate Ethyl N-[N-(3,5-dichloro-4-(1,1,2,3,3,3-hexafluoro-1-propoxy)-phenyl)-carbamoyl]-2,6-difluorobenzthiocarboximidate Ethyl N-[N-(3,5-dichloro-4-(1,1,2,2-tetrafluoroethoxy)-phenyl)-thiocarbamoyl]-2,6-difluorobenzthiocarboximidate Ethyl N-[N-(4-(2-chloro-1,1,2-trifluoroethoxy)-3,5-dichlorophenyl)-thiocarbamoyl]-2,6-difluorobenzthiocarboximidate Ethyl N-[N-(3,5-dichloro-4-(1,1,2,3,3,3-hexafluoro-1-propoxy)-phenyl)-thiocarbamoyl]-2,6-difluorobenzthiocarboximidate Ethyl N-[N-(3,5-dichloro-4-(difluoromethoxy)-2-fluorophenyl)-carbamoyl]-2-fluorobenzcarboximidate Ethyl N-[N-(4-chlorodifluoromethoxy-3,5-dichloro-2-fluorophenyl)-carbamoyl]-2,6-difluorobenzcarboximidate Ethyl N-[N-(3,5-dichloro-2-fluoro-4-trifluoromethoxyphenyl)-carbamoyl]-2,6-difluorobenzcarboximidate Ethyl N-[N-(4-(2-bromo-1,1,2-trifluoroethoxy)-3,5-dichloro-2-fluorophenyl)-carbamoyl]-2,6-difluorobenzcarboximidate Ethyl N-[N-(4-(2-chloro-1,1,2-trifluoroethoxy)-3,5-dichloro-2-fluorophenyl)-carbamoyl]-2-fluorobenzcarboximidate Ethyl N-[N-(4-(2-chloro-1,1,2-trifluoroethoxy)-3,5-dichloro-2-fluorophenyl)-carbamoyl]-2-chlorobenzcarboximidate Ethyl N-[N-(4-(2-chloro-1,1,2-trifluoroethoxy)-3,5-dichloro-2-fluorophenyl)-carbamoyl]-2,4-difluorobenzcarboximidate Ethyl N-[N-(4-(2-chloro-1,1,2-trifluoromethoxy)-3,5-dichloro-2-fluorophenyl)-carbamoyl]-2,6-difluorobenzcarboximidate Ethyl N-[N-(4-(2-chloro-1,1,2-trifluoroethoxy)-3,5-dichloro-2-fluorophenyl)-carbamoyl]-4-chloro-2-fluorobenzcarboximidate Ethyl N-[N-(4-(2-chloro-1,1,2-trifluoroethoxy)-3,5-dichloro-2-fluorophenyl)-carbamoyl]-2-chloro-4-fluorobenzcarboximidate Ethyl N-[N-(4-(2-chloro-1,1,2-trifluoroethoxy)-3,5-dichloro-2-fluorophenyl)-carbamoyl]-2,4-dichlorobenzcarboximidate Ethyl N-[N-(4-(2-chloro-1,1,2-trifluoroethoxy)-3,5-dichloro-2-fluorophenyl)-carbamoyl]-2-difluoromethoxybenzcarboximidate Ethyl N-[N-(4-(2-chloro-1,1,2-trifluoroethoxy)-3,5-dichloro-2-fluorophenyl)-carbamoyl]-2-(2,2,2-trifluoroethoxy)-benzcarboximidate Ethyl N-[N-(3,5-dichloro-2-fluoro-4-(1,1,2,2-tetrafluoroethoxy)-phenyl)-carbamoyl]-2-fluorobenzcarboximidate Ethyl N-[N-(3,5-dichloro-2-fluoro-4-(1,1,2,2-tetrafluoroethoxy)-phenyl)-carbamoyl]-2-chlorobenzcarboximidate Ethyl N-[N-(3,5-dichloro-2-fluoro-4-(1,1,2,2-tetrafluoroethoxy)-phenyl)-carbamoyl]-2,6-difluorobenzcarboximidate Ethyl N-[N-(3,5-dichloro-2-fluoro-4-(1,1,2,2-tetrafluoroethoxy)-phenyl)-carbamoyl]-2,4-dichlorobenzcarboximidate Ethyl N-[N-(3,5-dichloro-2-fluoro-4-(1,1,2,3,3,3-hexafluoro-1-propoxy)-phenyl)-carbamoyl]-2-fluorobenzcarboximidate Ethyl N-[N-(3,5-dichloro-2-fluoro-4-(1,1,2,3,3,3-hexafluoro-1-propoxy)-phenyl)-carbamoyl]-2-chlorobenzcarboximidate Ethyl N-[N-(3,5-dichloro-2-fluoro-4-(1,1,2,3,3,3-hexafluoro-1-propoxy)-phenyl)-carbamoyl]-2,6-difluorobenzcarboximidate Ethyl N-[N-(3,5-dichloro-2-fluoro-4-(1,1,2,3,3,3-hexafluoro-1-propoxy)-phenyl)-carbamoyl]-2,4-dichlorobenzcarboximidate Ethyl N-[N-(3,5-dichloro-2,4-difluorophenyl)-carbamoyl]-2-fluorobenzcarboximidate Ethyl N-[N-(3,5-dichloro-2,4-difluorophenyl)-carbamoyl]-2-chlorobenzcarboximidate Ethyl N-[N-(3,5-dichloro-2,4-difluorophenyl)-carbamoyl]-2,4-difluorobenzcarboximidate Ethyl N-[N-(3,5-dichloro-2,4-difluorophenyl)-carbamoyl]-4-chloro-2-fluorobenzcarboximidate Ethyl N-[N-(3,5-dichloro-2,4-difluorophenyl)-carbamoyl]-5-chloro-2-fluorobenzcarboximidate Ethyl N-[N-(3,5-dichloro-2,4-difluorophenyl)-carbamoyl]-2-chloro-6-fluorobenzcarboximidate Ethyl N-[N-(3,5-dichloro-2,4-difluorophenyl)-carbamoyl]-2-chloro-4-fluorobenzcarboximidate Ethyl N-[N-(3,5-dichloro-2,4-difluorophenyl)-carbamoyl]-2-chloro-5-fluorobenzcarboximidate Ethyl N-[N-(3,5-dichloro-2,4-difluorophenyl)-carbamoyl]-2,4-dichlorobenzcarboximidate Ethyl N-[N-(3,5-dichloro-2,4-difluorophenyl)-carbamoyl]-2,6-dichlorobenzcarboximidate Ethyl N-[N-(3,5-dichloro-2,4-difluorophenyl)-carbamoyl]-2-difluoromethoxybenzcarboximidate Ethyl N-[N-(3,5-dichloro-2,4-difluorophenyl)-carbamoyl]-2-(2,2,2-trifluoroethoxy)-benzcarboximidate Ethyl N-[N-(3,5-dichloro-2,4-difluorophenyl)-carbamoyl]-2,6-dimethoxybenzcarboximidate Ethyl N-[N-(3,5-dichloro-2,4-difluorophenyl)-carbamoyl]-2-difluoromethylmercaptobenzcarboximidate Ethyl N-[N-(2,3,4,5-tetrafluorophenyl)-carbamoyl]-2-fluorobenzcarboximidate Ethyl N-[N-(2,3,4,5-tetrafluorophenyl)-carbamoyl]-2,4-difluorobenzcarboximidate Ethyl N-[N-(2,3,4,5-tetrafluorophenyl)carbamoyl]-2,4-dichlorobenzcarboximidate Ethyl N-[N-(2,3,4,5-tetrafluorophenyl)-carbamoyl]-2-chloro-4-fluorobenzcarboximidate Ethyl N-[N-(2,3,4,5-tetrafluorophenyl)-carbamoyl]-2-chloro-5-fluorobenzcarboximidate Ethyl N-[N-(2,3,4,5-tetrafluorophenyl)-carbamoyl]-4-chloro-2-fluorobenzcarboximidate Ethyl N-[N-(2,4-dichloro-3-difluoromethyl-5-trifluoromethylphenyl)-carbamoyl]-2-fluorobenzcarboximidate Ethyl N-[N-(2,4-dichloro-3-difluoromethyl-5-trifluoromethylphenyl)-carbamoyl]-2-chlorobenzcarboximidate Ethyl N-[N-(2,4-dichloro-3-difluoromethyl-5-trifluoromethylphenyl)-carbamoyl]-2-chloro-6-fluorobenzcarboximidate Ethyl N-[N-(2,4-dichloro-3-difluoromethyl-5-trifluoromethylphenyl)-carbamoyl]-2,6-dichlorobenzcarboximidate Ethyl N-[N-(4-difluoromethoxy-2,3,5-trichlorophenyl)-carbamoyl]-2,6-difluorobenzcarboximidate Ethyl N-[N-(4-chlorodifluoromethoxy-2,3,5-trichlorophenyl)-carbamoyl]-2,6-difluorobenzacarboximidate Ethyl N-[N-(2,3,5-trichloro-4-trifluoromethoxyphenyl)-carbamoyl]-2,6-difluorobenzcarboximidate Ethyl N-[N-(4-(2-bromo-1,1,2-trifluoroethoxy)-2,3,5-trichlorophenyl)-carbamoyl]-2,6-difluorobenzcarboximidate Ethyl N-[N-(4-(2-chloro-1,1,2-trifluoroethoxy)-2,3,5-trichlorophenyl)-carbamoyl]-2-fluorobenzcarboximidate Ethyl N-[N-(4-(2-chloro-1,1,2-trifluoroethoxy)-2,3,5-trichlorophenyl)-carbamoyl]-2-chlorobenzcarboximidate Ethyl N-[N-(4-(2-chloro-1,1,2-trifluoroethoxy)-2,3,5-trichlorophenyl)-carbamoyl]-2,6-difluorobenzcarboximidate Ethyl N-[N-(4-(2-chloro-1,1,2-trifluoroethoxy)-2,3,5-trichlorophenyl)-carbamoyl]-2-chloro-4-fluorobenzcarboximidate Ethyl N-[N-(4-(2-chloro-1,1,2-trifluoroethoxy)-2,3,5-trichlorophenyl)-carbamoyl]-2,4-dichlorobenzcarboximidate Ethyl N-[N-(4-(1,1,2,2-tetrafluoroethoxy-2,3,5-trichlorophenyl)-carbamoyl]-2-fluorobenzcarboximidate Ethyl N-[N -(4-(1,1,2,2-tetrafluoroethoxy-2,3,5-trichlorophenyl)-carbamoyl]-2-chlorobenzcarboximidate Ethyl N-[N-(4-(1,1,2,2-tetrafluoroethoxy-2,3,5-trichlorophenyl)-carbamoyl]-2,6-difluorobenzcarboximidate Ethyl N-[N-(4-(1,1,2,2-tetrafluoroethoxy-2,3,5-trichlorophenyl)-carbamoyl]-2-chloro-4-fluorobenzcarboximidate Ethyl N-[N-(4-(1,1,2,2-tetrafluoroethoxy-2,3,5-trichlorophenyl)-carbamoyl]-2,4-dichlorobenzcarboximidate Ethyl N-[N-(4-(1,1,2,3,3,3-hexafluoro-1-propoxy)-2,3,5-trichlorophenyl)-carbamoyl]-2-fluorobenzcarboximidate Ethyl N-[N-(b 4-(1,1,2,3,3,3-hexafluoro-1-propoxy)-2,3,5-trichlorophenyl)-carbamoyl]-2-chlorobenzcarboximidate Ethyl N-[N-(4-(1,1,2,3,3,3-hexafluoro-1-propoxy)-2,3,5-trichlorophenyl)-carbamoyl]-2-difluorobenzcarboximidate Ethyl N-[N-(4-(1,1,2,3,3,3-hexafluoro-1-propoxy)-2,3,5-trichlorophenyl)-carbamoyl]-2-chloro-4-fluorobenzcarboximidate Ethyl N-[N-(4-(1,1,2,3,3,3-hexafluoro-1-propoxy)-2,3,5-trichlorophenyl)-carbamoyl]-2,4-dichlorobenzcarboximidate Ethyl N-[N-(2,3,4,5-tetrachlorophenyl)-chlorophenyl)-carbamoyl]-2-chlorobenzcarboximidate Ethyl N-[N-(2,3,4,5-tetrachlorophenyl)-chlorophenyl)-carbamoyl]-2-fluorobenzcarboximidate Ethyl N-[N-(2,3,4,5-tetrachlorophenyl)-chlorophenyl)-carbamoyl]-4-chloro-2-fluorobenzcarboximidate Ethyl N-[N-(2,3,4,5-tetrachlorophenyl)-chlorophenyl)-carbamoyl]-2-chloro-6-fluorobenzcarboximidate Ethyl N-[N-(2,3,4,5-tetrachlorophenyl)-chlorophenyl)-carbamoyl]-2-chloro-4-fluorobenzcarboximidate Ethyl N-[N-(2,3,4,5-tetrachlorophenyl)-carbamoyl]-2,4-dichlorobenzcarboximidate Ethyl N-[N-(2,3,4,5-tetrachlorophenyl)-carbamoyl]-b 2,6-dichlorobenzcarboximidate Ethyl N-[N-(4-(2-chloro-1,1,2-trifluoroethoxy)-2,3,5-trimethylphenyl)-carbamoyl]-2-fluorobenzcarboximidate Ethyl N-[N-(4-(2-chloro-1,1,2-trifluoroethoxy)-2,3,5-trimethylphenyl)-carbamoyl]-2,6-difluorobenzcarboximidate Ethyl N-[N-(4-(2-chloro-1,1,2-trifluoroethoxy)-2,3,5-trimethylphenyl)-carbamoyl]-2,4-dichlorobenzcarboximidate Ethyl N-[N-(4-(1,1,2,2-tetrafluoroethoxy)-2,3,5-trimethylphenyl)-carbamoyl]-2-fluorobenzcarboximidate Ethyl N-[N-(4-(1,1,2,2-tetrafluoroethoxy)-2,3,5-trimethylphenyl)-carbamoyl]-2,6-difluorobenzcarboximidate Ethyl N-[N-(4-(1,1,2,2-tetrafluoroethoxy)-2,3,5-trimethylphenyl)-carbamoyl]-2,4-dichlorobenzcarboximidate Ethyl N-[N-(4-(1,1,2,3,3,3-hexafluoro-1-propoxy)-2,3,5-trimethylphenyl)-carbamoyl]-2-fluorobenzcarboximidate Ethyl N-[N-(4-(1,1,2,3,3,3-hexafluoro-1-propoxy)-2,3,5-trimethylphenyl)-carbamoyl]-2,6-difluorobenzcarboximidate Ethyl N-[N-(4-(1,1,2,3,3,3-hexafluoro-1-propoxy)-2,3,5-trimethylphenyl)-carbamoyl]-2,4-dichlorobenzcarboximidate Ethyl N-[N-(4-(1,2-dichloroethenyloxy)-2,3,5-trimethylphenyl)-carbamoyl]-2,6-difluorobenzcarboximidate Ethyl N-[N-(2,3,5,6-tetrafluorophenyl)-carbamoyl]-2-fluorobenzcarboximidate Ethyl N-[N-(2,3,5,6-tetrafluorophenyl)-carbamoyl]-2-chlorobenzcarboximidate Ethyl N-[N-(2,3,5,6-tetrafluorophenyl)-carbamoyl]-2-chloro-6-fluorobenzcarboximidate Ethyl N-[N-(2,3,5,6-tetrafluorophenyl)-carbamoyl]-2,6-dimethoxybenzcarboximidate Ethyl N-[N-(pentafluorophenyl)-carbamoyl]-2-fluorobenzcarboximidate Ethyl N-[N-(pentafluorophenyl)-carbamoyl]-2-chloro-6-fluorobenzcarboximidate Ethyl N-[N-(pentafluorophenyl)-carbamoyl]-2,6-dichlorobenzcarboximidate The present invention also relates to a process for the preparation of the compounds of the formula (I) which comprises (a) reacting substituted aryl(thio)carboximidic acid esters of the formula (II)

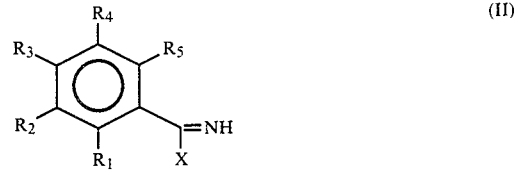

in which $R_1$ to $R_5$ and X have the same meanings as in formula (I), with compounds of the formula (III)

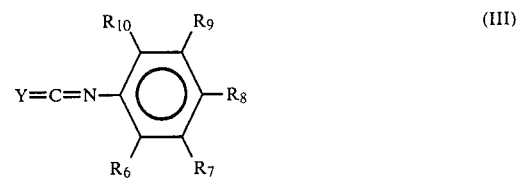

or with compounds of the formula (IV)

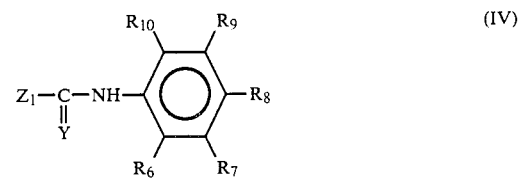

in which $R_6$ to $R_{10}$ and Y have the same meanings as in formula (I) and $Z_1$ denotes a basic leaving group other than halogen, such as, for example, $(C_1–C_3)$-alkoxy or phenoxy which can be halogenated, imidazole or triazole, or (b) reacting substituted aryl(thio)carboximidic acid ester derivatives of the formula (V)

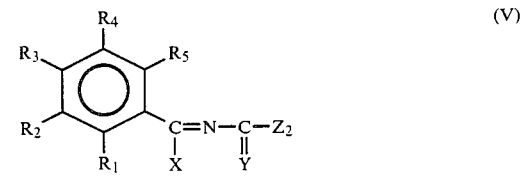

in which $R_1$ to $R_5$, X and Y have the same meanings as in formula (I) and $Z_2$ has the same meaning as $Z_1$ and additionally represents halogen, with substituted anilines of the formula (VI)

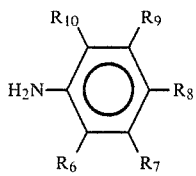

in which $R_6$ to $R_{10}$ have the same meanings as in formula (I), or (c) reacting substituted 1,3,5-oxadiazine derivatives of the formula (VII)

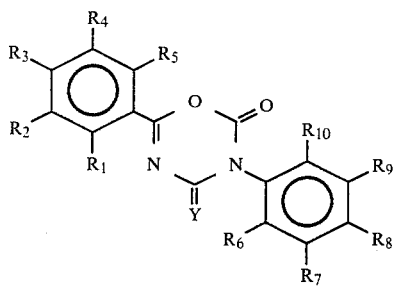

in which $R_1$ to $R_{10}$ and Y have the same meanings as in formula (I), with substituted hydroxy or mercapto compounds of the formulae (VIII) or (IX), respectively, $R_{11}OH$                                 (VIII)

$R_{12}SH$                                 (IX)

in which $R_{11}$ and $R_{12}$ have the same meanings as in formula (I).

The aryl(thio)carboximidic acid esters of the formula (II) to be used as the starting compounds in process of preparation (a) are in part novel and can be prepared by processes which are known per se from the literature:

1. By acid catalyzed or base-catalyzed addition of compounds of the formula (VIII) or (IX) to the substituted nitriles of the formula (X) in which $R_1$ to $R_5$ have the meaning indicated above.

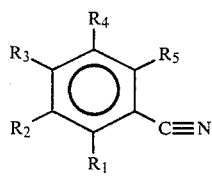

(see R. Rogers, Chem. Rev. 61, 179 (1961))

2. By transesterifying readily accessible benz(thio)-carboximidic acid esters of the formula (II) with compounds of the formula (VIII) or (IX) in which $R_1$ to $R_5$ and $R_{11}$ and $R_{12}$ have the meaning indicated above (R. J. Kauffmann, J. Am. Chem. Soc. 45, 1744 (1923)).

3. By O-alkylating or S-alkylating substituted (thio)-amides of the formula (XI) in which $R_1$ to $R_5$ and Y have the meaning indicated above

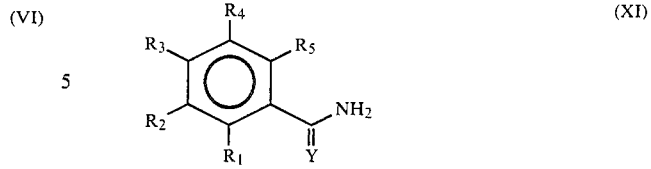

(M. Matsui, Brit. Chem. Abstract 98, 695 (1910) and H. Meerwein, J. prakt. Chem. 154, 154 (1940)).

The compounds of the formula (III) and (IV) to be used as the starting compounds in the process of preparation (a) are either known or can be prepared analogously to processes known from the literature (Houben-Weyl, Volume VIII, 1952; Houben-Weyl, Volume E 4, 1983).

The substituted arylcarboximido(thio)ester derivatives of the formula (V) to be used as the starting compounds in process of preparation (b) are accessible in a manner known per se from compounds of the formula (II) (Houben-Weyl, Volume E 4, 1983). The aniline of the formula (VI) required for route (b) are either known or can be prepared by processes known per se from the literature (Houben-Weyl, Volume XI/1 (1957)).

The 1,3,5-oxadiazine derivatives of the formula (VII) to be used as the starting compounds in process of preparation (c) are obtainable by processes known per se from the literature (U.S. Pat. No. 4,150,158).

The process variant (a), mentioned for the preparation of N-amino(thio)carbonylarylbenz(thio)carboximidic acid esters of the formula (I), is carried out with, or preferably without, a diluent. Suitable diluents are virtually all aprotic solvents. These include, in particular, aliphatic and aromatic and, if appropriate, halogenated hydrocarbons, such as pentane, hexane, heptane, cyclohexane, petroleum ether, gasoline, ligroin, benzene, toluene, xylene, methylene chloride, ethylene chloride, chloroform, carbon tetrachloride, chlorobenzene and o-dichlorobenzene, ethers, such as diethyl and dibutyl ethers, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methylpyrrolidone, and dimethyl sulfoxide, tetramethylene sulfone and hexamethylphosphoric triamide.

The reaction temperature is, in general, between $-10°$ C. and $+150°$ C., preferably between $+10°$ C. and 105° C.

The starting materials are usually employed in equimolar amounts. An excess of either reactant is, however, possible.

In process variant (b), the reaction is preferably carried out in a diluent. Suitable diluents are all neutral, non-nucleophilic organic solvents, but preferably those mentioned for process (a).

The reaction temperature is, in general, between $-10°$ C. and $+140°$ C., preferably between $+10°$ C. and $+80°$ C.

As in process (a), the starting materials are usually employed in equimolar amounts. An excess of either reactant is, however, possible.

In the preparation of the compounds of the formula (I) by process variant (c), the reaction of the compounds of the formula (VII) with the components (VIII) is advantageously carried out in an excess of the component (VIII).

In the reaction of substances of the formula (VII) with compounds of the formula (IX), equimolar amounts are usually employed and the reaction is advantageously carried out in a diluent which has already been mentioned under process variant (a).

The reaction temperature is, in general, between +20° C. and +150° C., preferably between +50° C. and +100° C.

The isolation and, if required, purification of the compounds of the formula (I) is effected by methods which are generally customary, for example by evaporating off the solvent (if appropriate under reduced pressure) and subsequently recrystallizing the residue, or by chromatography.

The compounds of the formula (I) are obtained in these reactions as E-isomers or Z-isomers or E/Z-mixtures. The E/Z-mixtures can be separated by physical processes known per se, such as fractional crystallization. Both isomers are biologically active and both are therefore embraced by the present invention.

The compounds of the formula (I) are readily soluble in most organic solvents.

The active compounds are well tolerated by plants and have an advantageous toxicity to warm-blooded animals and are suitable for controlling animal pests, in particular insects, arachnids and nematodes, and very particularly preferentially for controlling insects which occur in agriculture, in forestry, in the protection of stocks and materials and in the field of hygiene. They are effective against normally sensitive and resistant species and against all or individual stages of development. The pests mentioned above include the following:

From the order of the Isopoda, for example *Oniscus asellus, Armadillidium vulgare* and *Porcellio scaber.*

From the order of Diplopoda, for example *Blaniulus guttulatus.*

From the order of Chilopoda, for example *Geophilus carpophagus* and Scutigera species.

From the order of Symphyla, for example *Scutigerella immaculata.*

From the order of Thysanura, for example *Lepisma saccharina.*

From the order of Collembola, for example *Onychiurus armatus.*

From the order of Orthoptera, for example *Blatta orientalis, Periplaneta americana, Leucophaea maderae, Blatella germanica, Acheta domesticus,* Gryllotalpa species, *Locusta migratoria migratorioides, Melanoplus differentialis* and *Schistocerca gregaria.*

From the order of Dermaptera, for example *Forficula auricularia.*

From the order of Isoptera, for example Reticulitermes species.

From the order of Anoplura, for example *Phylloera vastatrix,* Phemphigus species, *Pediculus humanus corporis,* Haematopinus species and Linognathus species.

From the order of Mallophaga, for example Trichodectes species and Damalinea species.

From the order of Thysanoptera, for example *Hercinothrips femoralis* and *Thrips tabaci.*

From the order of Heteroptera, for example Eurygaster species, *Dysdercus intermedius, Piesma quadrata, Cimex Lectularius, Rhodnius prolixus* and Triatoma species.

From the order of Homoptera, for example *Aleurodes brassicae, Bemisia tabaci, Trialeurodes vaporariorum, Aphis gossypii, Bravicornyne brassicae, Cryptomyzus ribis, Doralis fabae, Doralis pomi, Eriosoma lanigerum, Hyalopterus arundinis, Macrosiphium avenae,* Myzus species, *Phorodon humuli, Rhopalosiphum padi,* Empoasca species, *Euscelus bilobatus, Nephotettix cincticeps, Lecanium corni, Saissetia oleae, Laodelphax striatellus, Nilaparvata lugens, Aonidiella auroantii, Aspidiotus hederae,* Pseudococcus species and Psylla species.

From the order of Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria species, *Buceulatrix thurberiella, Phyllocnistis citrella,* Agrotis species, Euxoa species, Feltia species, *Earias insulana,* Heliothis species, *Laphygma exigua, Mamestra brassicae, Panolis flammea, Prodenia litura,* Spodoptera species, *Trichoplusia ni, Carpocapsa pomonella,* Pieris species, Chilo species, *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana.*

From the order of Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochlearieae,* Diabrotica species, *Psylliodes chrysocephala, Epilachna varivestis,* Atomaria species, *Oryzaephilus surinamensis,* Anthonomus species, Sitophilus species, *Otiorrhynchus sulcatus, Cosmopolites sordidus, Ceuthorrhynchus assimilis, Hypera postica,* Dermestes species, Trogoderma species, Anthrenus species, Attagenus species, Lyctus species, *Meligethes aeneus,* Ptinus species, *Niptus hololeucus, Gibbium psylloides,* Tribolium species, *Tenebrio molitor,* Agriotes species, Conoderus species, *Melolontha melolontha, Amiphimallon solstitialis* and *Costelytra zealandica.*

From the order of Hymenoptera, for example Diprion species, Hoplocampa species, Lasius species, *Monomorium pharaonis* and Vespa species.

From the order of Diptera, for example Aedes species, Anopheles species, Culex species, *Drosophila melanogaster,* Musca species, Fannia species, *Calliphora erythrocephala,* Lucilia species, Chrysomyia species, Cuterebra species, Gastrophilus species, Hyppobosca species, Stomoxys species, Oestrus species, Hypoderma species, Tabanus species, Tannia species, *Bibio hortulanus, Oscinella frit,* Phorbia species, *pegomyia hyoscyami, Ceratitis capitata, Dacus oleae* and *Tipula paludosa.*

From the order of Siphonaptera, for example *Xenopsylla cheopis* and Ceratophyllus species.

From the order of Arachnida, for example *Scorpio maurus* and *Latrodectus mactans.*

The invention also relates to agents containing the compounds of the formula I as well as suitable formulation auxiliaries.

The agents according to the invention generally contain 1–95% by weight of the active compounds of the formula I. They can be applied in the customary preparations in the form of wettable powders, emulsifiable concentrates, sprayable solutions, dusting agents or granules.

Wettable powders are preparations which can be dispersed uniformly in water and which, in addition to the active compound and also a diluent or inert substance, also contain wetting agents, for example polyoxyethylated alkylphenols, polyoxyethylated fatty alcohols, alkylsulfonates or alkylphenolsulfonates, and dispersing agents, for example sodium ligninsulfonate, sodium 2,2'-dinaphthylmethane-6,6'-disulfonate, sodium dibutylnaphthalenesulfonate or sodium oleylmethyltaurate.

Emulsifiable concentrates are prepared by dissolving the active compound in an organic solvent, for example butanol, cyclohexanone, dimethylformamide, xylene or higher-boiling aromatic compounds or hydrocarbons, with the addition of one or more emulsifier. The following are examples of emulsifiers which can be used: calcium salts of alkylarylsulfonic acids, such as Ca dodecylbenzenesulfonate, or nonionic emulsifier, such as fatty acid polyglycol esters, alkylaryl polyglycol ethers, fatty alcohol polyglycol ethers, propylene oxide/ethylene oxide condensation products, alkyl polyethers, fatty acid esters of sorbitan, fatty acid esters of polyoxyethylenesorbitan or esters of polyoxyethylenesorbitol.

Dusting agents are obtained by grinding the active compound with finely divided solid substances, for example talc, natural clays, such as kaolin, bentonite or pyrophillite, or diatomaceous earth. Granules can be prepared either by spraying the active compound onto an adsorptive, granulated inert material or by applying active compound concentrates by means of adhesives, for example polyvinyl alcohol, sodium polyacrylate or mineral oils, to the surface of carriers, such as sand, kaolinite or granulated inert material. It is also possible to prepare suitable active compounds in the manner customary for the production of fertilizer granules—if desired as a mixture with fertilizers.

In their commercially available formulations and in the application forms prepared from these formulations, the active compounds according to the invention can be in the form of a mixture with other active compounds, such as insecticides, attractants, sterilizers, acaricides, nematocides, fungicides, growth-regulating substances or herbicides. Insecticides include, for example: phosphoric acid esters, carbamates, carboxylic acid esters, chlorinated hydrocarbons, phenylureas, substances produced by microorganisms, and others.

The content of active compound in the application forms prepared from the commercially available formulations can vary within wide ranges. The concentration of active compound in the application forms can be from 0.0000001 to 100% by weight of active compound, preferably between 0.00001 and 1% by weight.

Application is effected in a customary manner suited to the application forms.

The active compounds according to the invention are also suitable for controlling ectoparasites and endoparasites, preferably ectoparasitic insects in the field of veterinary medicine or in the field of animal husbandry.

The application of the active compounds according to the invention is effected in this case in a known manner, such as by oral administration in the form of, for example, tablets, capsules, drink or granules, dermal application in the form of, for example, dipping, spraying, pouring on and spotting on and powdering on, and parenteral administration in the form of, for example, injection.

The new compounds, according to the invention, of the formula I can accordingly also be employed with particular advantage in animal husbandry (for example cattle, sheep, pigs and poultry, such as chickens, geese and the like). In a preferred embodiment of the invention, the new compounds, if appropriate in suitable formulations (cf. above) and, if appropriate, together with the drinking water or feed, are administered to the animals orally. Since excretion in the feces takes place in an effective manner, the development of insects in the feces of the animals can be prevented very simply in this manner. The dosages and formulations suitable in a particular case depend particularly on the nature and stage of development of the livestock and on the intensity of infestation by insects, and can be determined and established easily by the customary methods. In the case of cattle, for example, the new compounds can be employed in dosage amounts of 0.01 to 1 mg/kg of body weight.

The following Examples serve to illustrate the invention.

A. FORMULATION EXAMPLES (a) A dusting agent is obtained by mixing 10 parts by weight of active compound and 90 parts by weight of talc as an inert substance, and comminuting the mixture in a beater mill.

(b) A wettable powder which is readily dispersible in water is obtained by mixing 25 parts by weight of active compound, 65 parts by weight of kaolin-containing quartz as an inert substance, 10 parts by weight of potassium ligninsulfonate and 1 part by weight of sodium oleoylmethyltaurate as a wetting and dispersing agent, and grinding the mixture in a pinned disc mill.

(c) A dispersion concentrate which is readily dispersible in water is prepared by mixing 20 parts by weight of active compound with 6 parts by weight of an alkylphenol polyglycol ether (Triton×207), 3 parts by weight of isotridecanol polyglycol ether (8 EO) and 71 parts by weight of a paraffinic mineral oil (boiling range, for example, approx. 255° to over 377° C.), and grinding the mixture in an abrasion ball mill to a fineness of less than 5 microns.

(d) An emulsifiable concentrate can be prepared from 15 parts by weight of active compound, 75 parts by weight of cyclohexanone as solvent and 10 parts by weight of oxyethylated nonylphenol (10 EO) as an emulsifier.

(e) Granules can be prepared from 2 to 15 parts by weight of active compound and an inert granular carrier, such as attapulgite, pumice granules and/or quartz sand.

B. Chemical Examples

| Example No. | R¹ | R² | R³ | R⁴ | R⁵ | R⁶ | R⁷ | R⁸ | R⁹ | R¹⁰ | X | Y | M.P. (°C.) of E/Z-mixture |
|---|---|---|---|---|---|---|---|---|---|---|---|---|---|
| 1 | F | H | H | H | F | F | H | H | H | H | OC₂H₅ | O | 93-95 |
| 2 | OCH₃ | H | H | H | OCH₃ | F | H | H | H | H | OC₂H₅ | O | 143-145 |
| 3 | F | H | H | H | H | H | H | H | H | H | OC₂H₅ | O | 77 |
| 4 | H | H | H | H | F | OC₂H₅ | OCF₂CHF₂ | H | H | H | OC₂H₅ | O | 62 |
| 5 | F | H | H | H | Cl | H | NO₂ | H | H | H | OC₂H₅ | O | 128 |
| 6 | F | H | H | H | H | H | NO₂ | H | H | H | OC₂H₅ | O | 110 |
| 7 | F | H | H | H | H | H | —NH—CH(CF₃)₂ | H | H | H | OC₂H₅ | O | 94 |
| 8 | F | H | H | H | H | H | COOCH₃ | H | H | H | OC₂H₅ | O | 100 |
| 9 | F | H | H | H | H | H | CHF₂ | H | H | H | OC₂H₅ | O | 102 |
| 10 | F | H | H | H | H | H | CF₃ | H | H | H | OC₂H₅ | O | 120 |
| 11 | H | H | H | H | H | H | H | F | H | H | OC₂H₅ | O | 78-80 |
| 12 | H | H | H | H | H | H | H | Cl | H | H | OC₂H₅ | O | 128 |
| 13 | F | H | H | H | F | H | H | Cl | H | H | OC₂H₅ | O | 114 |
| 14 | F | H | H | H | Cl | H | H | Cl | H | H | OCH₂C≡CH | O | 130-132 |
| 15 | Cl | H | H | H | H | H | H | OCHF₂ | H | H | OC₂H₅ | O | 109 |
| 16 | F | H | H | H | H | H | H | OCHF₂ | H | H | OC₂H₅ | O | 80 |
| 17 | F | H | H | H | Cl | H | H | OCHF₂ | H | H | OC₂H₅ | O | 89 |
| 18 | Cl | H | H | H | Cl | H | H | OCHF₂ | H | H | OC₂H₅ | O | 88 |
| 19 | F | H | H | H | H | H | H | OCClF₂ | H | H | OC₂H₅ | O | 95 |
| 20 | F | H | H | H | H | H | H | OCF₃ | H | H | OC₂H₅ | O | 93-95 |
| 21 | F | H | H | H | H | H | H | OCF₃ | H | H | OC₂H₅ | O | 85 |
| 22 | F | H | H | H | H | H | H | OCF₃ | H | H | OCH₃ | O | 125-127 |
| 23 | F | H | H | H | H | H | H | OCF₃ | H | H | OC₂H₅ | O | 97-99 |
| 24 | F | H | H | H | H | H | H | OCF₃ | H | H | O(CH₂)₂CH₃ | O | 84 |
| 25 | F | H | H | H | H | H | H | OCF₃ | H | H | O(CH₂)₃CH₃ | O | 105 |
| 26 | F | H | H | H | H | H | H | OCF₃ | H | H | O(CH₂)₅CH₃ | O | 69-71 |
| 27 | F | H | H | H | H | H | H | OCF₃ | H | H | cyclohexyl-O | O | 130-132 |
| 28 | H | F | H | H | H | H | H | OCF₃ | H | H | OC₂H₅ | O | 56 |
| 29 | Cl | H | H | H | H | H | H | OCF₃ | H | H | OC₂H₅ | O | 86-87 |
| 30 | H | H | Cl | H | H | H | H | OCF₃ | H | H | OC₂H₅ | O | 110 |
| 31 | I | H | H | H | H | H | H | OCF₃ | H | H | OC₂H₅ | O | 115 |
| 32 | F | H | F | H | F | H | H | OCF₃ | H | H | OC₂H₅ | O | 91 |
| 33 | F | H | H | Cl | F | H | H | OCF₃ | H | H | OC₂H₅ | O | 90-99 |
| 34 | F | H | H | H | F | H | H | OCF₃ | H | H | O(CH₂)₅CH₃ | O | 71 |
| 35 | F | H | Cl | H | H | H | H | OCF₃ | H | H | OC₂H₅ | O | 99 |
| 36 | F | H | H | H | Cl | H | H | OCF₃ | H | H | OC₂H₅ | O | 113 |
| 37 | F | H | H | H | H | H | H | OCF₃ | H | H | OC₂H₅ | O | 88 |
| 38 | Cl | H | F | H | H | H | H | OCF₃ | H | H | OC₂H₅ | O | 79 |

-continued

B. Chemical Examples

| Example No. | R¹ | R² | R³ | R⁴ | R⁵ | R⁶ | R⁷ | R⁸ | R⁹ | R¹⁰ | X | Y | M.P. (°C.) of E/Z-mixture |
|---|---|---|---|---|---|---|---|---|---|---|---|---|---|
| 39 | Cl | H | H | F | H | H | H | OCF₃ | H | H | OC₂H₅ | O | 92 |
| 40 | Cl | H | Cl | H | H | H | H | OCF₃ | H | H | OC₂H₅ | O | 91 |
| 41 | Cl | H | H | Cl | H | H | H | OCF₃ | H | H | OC₂H₅ | O | 110 |
| 42 | Cl | H | H | H | Cl | H | H | OCF₃ | H | H | OC₂H₅ | O | 99–102 |
| 43 | F | F | F | H | F | H | H | OCF₃ | H | H | OC₂H₅ | O | 123–125 |
| 44 | Cl | H | H | H | OCH₃ | H | H | OCF₃ | H | H | OC₂H₅ | O | 130 |
| 45 | F | H | H | NO₂ | H | H | H | OCF₃ | H | H | OC₂H₅ | O | 102–105 |
| 46 | Cl | H | H | NO₂ | H | H | H | OCF₃ | H | H | OC₂H₅ | O | 150 |
| 47 | CH₃SO₂O— | H | H | H | H | H | H | OCF₃ | H | H | OC₂H₅ | O | 94–96 |
| 48 | CHF₂O— | H | H | H | H | H | H | OCF₃ | H | H | OC₂H₅ | O | 87 |
| 49 | H | H | CF₃O— | H | H | H | H | OCF₃ | H | H | OC₂H₅ | O | 97 |
| 50 | H | CF₃O— | H | H | H | H | H | OCF₃ | H | H | OC₂H₅ | O | 82 |
| 51 | CH₃O— | H | H | H | H | H | H | OCF₃ | H | H | OC₂H₅ | O | 104 |
| 52 | H | H | CCl₃CF₂O— | H | H | H | H | OCF₃ | H | H | OC₂H₅ | O | 118 |
| 53 | CHF₂S— | H | H | H | H | H | H | OCF₃ | H | H | OC₂H₅ | O | 92 |
| 54 | H | NO₂ | H | CF₃ | H | H | H | OCF₃ | H | H | OC₂H₅ | O | 153 |
| 55 | CF₃ | H | H | H | H | H | H | OCF₃ | H | H | OC₂H₅ | O | 95–98 |
| 56 | H | CF₃ | H | H | H | H | H | OCF₃ | H | H | OCH₃ | O | 160 |
| 57 | CH₃ | H | H | H | H | H | H | OCF₃ | H | H | OC₂H₅ | O | 113 |
| 58 | H | H | H | H | H | H | H | OCF₂CHF₂ | H | H | OC₂H₅ | O | 101–103 |
| 59 | H | H | H | H | H | H | H | OCF₂CHF₂ | H | H | OCH₂C≡CH | O | 137–139 |
| 60 | F | H | H | H | H | H | H | OCF₂CHF₂ | H | H | OCH₂CF₃ | O | 116 |
| 61 | F | H | H | H | H | H | H | OCF₂CHCl₂ | H | H | OC₂H₅ | O | 114–116 |
| 62 | F | H | H | H | H | H | H | —OC=CH\|\|Cl Cl | H | H | OC₂H₅ | O | 106–108 |
| 63 | F | H | H | H | F | H | H | —SCF₃ | H | H | OC₂H₅ | O | 96–98 |
| 64 | F | H | H | H | H | H | H | —SCF₂CHClF | H | H | OC₂H₅ | O | 89 |
| 65 | F | H | H | H | F | H | H | —SO₂CF₃ | H | H | OC₂H₅ | O | 112 |
| 66 | F | H | H | H | H | H | H | NO₂ | H | H | OC₂H₅ | O | 155 |
| 67 | Cl | H | H | H | H | H | H | NO₂ | H | H | OC₂H₅ | O | 161 |
| 68 | F | H | H | H | Cl | H | H | NO₂ | H | H | OC₂H₅ | O | 165 |
| 69 | Cl | H | H | H | Cl | H | H | NO₂ | H | H | OC₂H₅ | O | 160–162 |
| 70 | F | H | H | H | H | H | H | CF₃ | H | H | OC₂H₅ | O | 170 |
| 71 | Cl | H | H | H | H | H | H | CF₃ | H | H | OC₂H₅ | O | 131 |
| 72 | Cl | H | H | H | Cl | H | H | CF₃ | H | H | OC₂H₅ | O | 115 |
| 73 | F | H | H | H | F | H | H | —C(CF₃)₂OH | H | H | OC₂H₅ | O | 122–125 |
| 74 | F | H | H | H | H | H | H | —C(CF₃)₂OH | H | H | OC₂H₅ | O | oil |
| 75 | F | H | H | H | H | H | H | COOCH₃ | H | H | OC₂H₅ | O | oil |
| 76 | F | H | H | H | H | H | H | C₂H₅ | H | H | OC₂H₅ | O | 165 |
| 77 | F | H | H | H | H | H | H | —C(CH₃)₃ | H | H | OC₂H₅ | O | 116 |
| 78 | F | H | H | H | H | H | H | Cl | H | H | OC₂H₅ | O | 165 |
| 79 | Cl | H | H | H | H | H | H | OCF₃ | H | H | OC₂H₅ | O | 134 |
| 80 | F | H | H | H | H | H | H | OCF₃ | H | H | SCH₃ | S | 134 |
| 81 | Cl | H | H | H | H | H | H | OCF₃ | H | H | SCH₃ | O | 131–132 |
| 82 | Cl | H | H | H | H | H | Cl | CF₃ | H | H | SCH₃ | O | 159–160 |
| 83 | F | H | H | H | H | Cl | Cl | H | H | H | OC₂H₅ | O | 105 |

-continued
B. Chemical Examples

| Example No. | R¹ | R² | R³ | R⁴ | R⁵ | R⁶ | R⁷ | R⁸ | R⁹ | R¹⁰ | X | Y | M.P. (°C.) of E/Z-mixture |
|---|---|---|---|---|---|---|---|---|---|---|---|---|---|
| 84 | F | H | H | H | H | Cl | CH₃ | H | H | H | OC₂H₅ | O | 110 |
| 85 | F | H | H | H | H | F | H | F | H | H | OC₂H₅ | O | 73 |
| 86 | F | H | F | H | H | F | H | F | H | H | OC₂H₅ | O | 71 |
| 87 | F | H | Cl | H | H | F | H | F | H | H | OC₂H₅ | O | 105–106 |
| 88 | F | H | H | Cl | Cl | F | H | F | H | H | OC₂H₅ | O | 103 |
| 89 | F | H | H | H | H | F | H | F | H | H | OC₂H₅ | O | 95 |
| 90 | Cl | H | F | H | H | F | H | F | H | H | OC₂H₅ | O | 97–99 |
| 91 | Cl | H | H | F | H | F | H | F | H | H | OC₂H₅ | O | 101 |
| 92 | F | H | H | H | H | Cl | H | Cl | H | H | OC₂H₅ | O | 136–138 |
| 93 | F | H | H | H | H | CF₃ | H | Cl | H | H | OC₂H₅ | O | 120 |
| 94 | F | H | H | H | H | OCF₂CHClF | H | —CH(CH₃)₂ | H | H | OC₂H₅ | O | 69 |
| 95 | F | H | H | H | F | H | H | OCF₂CHClF | H | H | OC₂H₅ | O | 121 |
| 96 | F | H | H | H | H | H | H | H | CF₃ | H | OC₂H₅ | O | 104 |
| 97 | CH₃O | H | H | H | CH₃O | F | H | H | F | H | OC₂H₅ | O | 140 |
| 98 | CH₃O | H | H | H | CH₃O | F | H | H | H | H | OC₂H₅ | O | 200 |
| 99 | CH₃O | H | H | H | CH₃O | H | H | H | H | Cl | OC₂H₅ | O | oil |
| 100 | CH₃O | H | H | H | CH₃O | CH₃ | H | H | H | CH₃ | OC₂H₅ | O | oil |
| 101 | CH₃O | H | H | H | H | CH₃ | H | H | H | C₂H₅ | OC₂H₅ | O | 95 |
| 102 | Cl | H | H | H | H | Cl | Cl | Cl | H | H | OC₂H₅ | O | 88 |
| 103 | H | H | H | H | H | H | Cl | Cl | H | H | OC₂H₅ | O | 145–147 |
| 104 | F | H | H | H | H | H | NO₂ | F | H | H | OC₂H₅ | O |  |
| 105 | F | H | H | H | F | H | F | 3,5-dimethylpiperidinyl | H | H | OC₂H₅ | O | oil |
| 106 | F | H | H | H | H | H | CF₃ | Cl | H | H | OC₂H₅ | O | 130 |
| 107 | Cl | H | H | H | H | H | Cl | OCF₂CHClF | H | H | OC₂H₅ | O | oil |
| 108 | F | H | H | H | H | H | Cl | OCF₂CHClF | H | H | OC₂H₅ | O | oil |
| 109 | F | H | H | F | H | H | Cl | OCF₂CHClF | H | H | OC₂H₅ | O | 78 |
| 110 | F | H | H | Cl | H | H | Cl | OCF₂CHClF | H | H | OC₂H₅ | O | 90 |
| 111 | Cl | H | H | F | Cl | H | Cl | OCF₂CHClF | H | H | OC₂H₅ | O | 70 |
| 112 | F | H | H | H | H | H | OCF₂CHClF | Cl | H | H | OC₂H₅ | O | 128–129 |
| 113 | F | H | H | H | H | H | OCF₂CHClF | Cl | H | H | OC₂H₅ | O | 110–111 |
| 114 | F | H | H | H | F | H | OCF₂CHClF | Cl | H | H | OC₂H₅ | O | 117 |
| 115 | F | H | H | H | H | H | OCF₂CHClF | Cl | H | H | OC₂H₅ | O | 123 |
| 116 | F | H | H | H | H | H | OCF₂CHF₂ | Cl | H | H | OC₂H₅ | O | 130–132 |
| 117 | F | H | H | H | H | H | Cl | COOC(CH₃)₃ | H | H | OC₂H₅ | O | oil |
| 118 | F | H | H | NO₂ | H | H | Cl | CH₃ | H | H | OC₂H₅ | O | 105 |
| 119 | F | F | H | H | H | H | Cl | Cl | H | H | OC₂H₅ | O | 96 |
| 120 | F | H | H | H | H | H | Cl | Cl | H | H | OC₂H₅ | O | 105 |
| 121 | H | H | H | H | H | H | Cl | Cl | H | H | OC₂H₅ | O | 109 |
| 122 | Cl | H | H | H | H | H | Cl | Cl | H | H | OC₂H₅ | O | 140 |
| 123 | Cl | H | Cl | H | H | H | Cl | Cl | H | H | OC₂H₅ | O | 120 |

-continued
B. Chemical Examples

| Example No. | $R^1$ | $R^2$ | $R^3$ | $R^4$ | $R^5$ | $R^6$ | $R^7$ | $R^8$ | $R^9$ | $R^{10}$ | X | Y | M.P. (°C.) of E/Z-mixture |
|---|---|---|---|---|---|---|---|---|---|---|---|---|---|
| 124 | Cl | H | H | Cl | H | H | Cl | Cl | H | H | $OC_2H_5$ | O | 124 |
| 125 | F | F | F | F | F | H | Cl | Cl | H | H | $OC_2H_5$ | O | 105 |
| 126 | H | $CF_3O$ | H | H | H | H | Cl | Cl | H | H | $OC_2H_5$ | O | 85 |
| 127 | H | H | $CF_3O$ | H | H | H | Cl | Cl | H | H | $OC_2H_5$ | O | 85 |
| 128 | $CH_3O$ | H | H | H | H | H | Cl | Cl | H | H | $OC_2H_5$ | O | 143 |
| 129 | H | $NO_2$ | H | $CF_3$ | H | H | Cl | Cl | H | H | $OC_2H_5$ | O | 139-141 |
| 130 | $CF_3$ | H | H | H | H | H | Cl | Cl | H | H | $OC_2H_5$ | O | 135 |
| 131 | H | $CF_3$ | H | H | H | H | Cl | Cl | H | H | $OCH_3$ | O | 118 |
| 132 | F | H | H | H | F | H | $OCHF_2$ | $OCHF_2$ | H | H | $OC_2H_5$ | O | oil |
| 133 | F | H | H | H | F | H | $CH_3$ | ―N⟨piperidine⟩ | H | H | $OC_2H_5$ | O | oil |
| 134 | F | H | H | H | H | H | $CH_3$ | $CH_3$ | H | H | $OC_2H_5$ | O | 89 |
| 135 | Cl | H | H | H | H | H | $CF_3$ | Cl | H | H | $SCH_3$ | O | 96-99 |
| 136 | F | H | H | H | H | H | Cl | Cl | H | H | $SCH_3$ | O | 125 |
| 137 | Cl | H | H | H | H | H | Cl | Cl | H | H | $SCH_3$ | O | 125 |
| 138 | F | H | H | H | H | H | $CF_3$ | H | Cl | H | $OC_2H_5$ | O | 98 |
| 139 | F | H | H | H | H | H | $CH_3$ | H | $CF_3$ | H | $OC_2H_5$ | O | 140 |
| 140 | F | H | H | H | H | H | $C_2H_5SO_2$― | H | $CH_3$ | H | $OC_2H_5$ | O | 77-80 |
| 141 | F | H | H | H | H | H | H | H | $CF_3$ | H | $OC_2H_5$ | O | 102 |
| 142 | F | H | H | H | H | F | H | F | Cl | H | $OC_2H_5$ | O | 85 |
| 143 | Cl | H | H | H | H | F | H | F | Cl | H | $OC_2H_5$ | O | 55 |
| 144 | F | H | H | H | F | F | H | F | Cl | H | $OC_2H_5$ | O | 120 |
| 145 | F | H | H | H | Cl | F | H | F | Cl | H | $OC_2H_5$ | O | 60 |
| 146 | Cl | H | H | H | F | F | H | F | Cl | H | $OC_2H_5$ | O | 92 |
| 147 | F | H | H | H | H | Cl | H | F | Cl | H | $OC_2H_5$ | O | 210 |
| 148 | F | H | H | H | H | H | H | $CH_3$ | Br | H | $OC_2H_5$ | O | 140 |
| 149 | F | H | H | H | H | H | H | Cl | Cl | H | $OC_2H_5$ | O | 128 |
| 150 | F | H | H | H | F | H | Cl | $OCF_2CHClF$ | $CH_3$ | H | $OC_2H_5$ | O | 164 |
| 151 | F | H | H | H | H | H | $CF_3$ | Cl | $CF_3$ | H | $OC_2H_5$ | O | oil |
| 152 | F | H | H | H | F | H | Cl | $OCHF_2$ | Cl | H | $OC_2H_5$ | O | 128 |
| 153 | F | H | H | H | H | H | Cl | $OCF_2CHClF$ | Cl | H | $OC_2H_5$ | O | 103-105 |
| 154 | F | H | H | H | F | H | Cl | $OCF_2CHClF$ | Cl | H | $OC_2H_5$ | O | 103-105 |
| 155 | F | H | H | H | Cl | H | Cl | $OCF_2CHClF$ | Cl | H | $OC_2H_5$ | O | 123-124 |
| 156 | F | H | H | H | H | H | Cl | $OCF_2CHBrF$ | Cl | H | $OC_2H_5$ | O | 110-112 |
| 157 | Cl | H | H | H | H | H | Cl | $OCF_2CHBrF$ | Cl | H | $OC_2H_5$ | O | 121-124 |
| 158 | F | H | H | H | F | H | Cl | $OCF_2CHBrF$ | Cl | H | $OC_2H_5$ | O | 96 |
| 159 | F | H | H | $NO_2$ | H | H | Cl | $OCF_2CHBrF$ | Cl | H | $OC_2H_5$ | O | 100-103 |
| 160 | Cl | H | H | H | Cl | H | Cl | $OCF_2CHBrF$ | Cl | H | $OC_2H_5$ | O | 118-120 |
| 161 | F | H | H | H | H | H | Cl | $OCF_2CHF_2$ | Cl | H | $OC_2H_5$ | O | 101-203 |
| 162 | F | H | H | H | H | H | Cl | $OCF_2CHF_2$ | Cl | H | $OCH_3$ | O | 110-113 |
| 163 | F | H | H | H | F | H | Cl | $OCF_2CHF_2$ | Cl | H | $OC_2H_5$ | O | 123-124 |
| 164 | F | H | H | H | Cl | H | Cl | $OCF_2CHF_2$ | Cl | H | $OC_2H_5$ | O | 113 |
| 165 | Cl | H | Cl | H | H | H | Cl | $OCF_2CHF_2$ | Cl | H | $OC_2H_5$ | O | 124-125 |
| 166 | H | H | H | H | H | H | Cl | $OCF_2CHF_2$ | Cl | H | $OC_2H_5$ | O | 155 |

-continued

B. Chemical Examples

| Example No. | $R^1$ | $R^2$ | $R^3$ | $R^4$ | $R^5$ | $R^6$ | $R^7$ | $R^8$ | $R^9$ | $R^{10}$ | X | Y | M.P. (°C.) of E/Z-mixture |
|---|---|---|---|---|---|---|---|---|---|---|---|---|---|
| 167 | F | H | H | H | F | H | Cl | OCF$_2$CHF$_2$ | Cl | H | OC$_2$H$_5$ | O | 120-121 |
| 168 | F | H | Cl | H | H | H | Cl | OCF$_2$CHF$_2$ | Cl | H | OC$_2$H$_5$ | O | 142 |
| 169 | F | H | H | Cl | H | H | Cl | OCF$_2$CHF$_2$ | Cl | H | OC$_2$H$_5$ | O | 149 |
| 170 | F | H | F | H | H | H | Cl | OCF$_2$CHF$_2$ | Cl | H | OC$_2$H$_5$ | O | 115-116 |
| 171 | Cl | H | H | H | CH$_3$O | H | Cl | OCF$_2$CHF$_2$ | Cl | H | OC$_2$H$_5$ | O | 132 |
| 172 | Cl | H | F | H | H | H | Cl | OCF$_2$CHF$_2$ | Cl | H | OC$_2$H$_5$ | O | 138 |
| 173 | Cl | H | Cl | H | Cl | H | Cl | OCF$_2$CHF$_2$ | Cl | H | OC$_2$H$_5$ | O | 135 |
| 174 | Cl | H | H | H | CH$_3$O | H | Cl | OCF$_2$CHF$_2$ | Cl | H | OC$_2$H$_5$ | O | 111-112 |
| 175 | CH$_3$O | H | H | H | H | H | Cl | OCF$_2$CHF$_2$ | Cl | H | OC$_2$H$_5$ | O | 104 |
| 176 | CH$_3$SO$_2$O— | H | H | H | H | H | Cl | OCF$_2$CHF$_2$ | Cl | H | OC$_2$H$_5$ | O | oil |
| 177 | CHF$_2$S— | H | H | H | H | H | Cl | OCF$_2$CHF$_2$ | Cl | H | OC$_2$H$_5$ | O | 91 |
| 178 | CH$_3$ | H | H | H | H | H | Cl | OCF$_2$CHF$_2$ | Cl | H | OC$_2$H$_5$ | O | 138 |
| 179 | F | H | H | H | H | H | Cl | OCF$_2$CHF$_2$ | Cl | H | O(CH$_2$)$_2$CH$_3$ | O | 118 |
| 180 | F | H | H | H | H | H | Cl | OCF$_2$CHF$_2$ | Cl | H | O(CH$_2$)$_3$CH$_3$ | O | 109 |
| 181 | F | H | H | H | H | H | Cl | OCF$_2$CHF$_2$ | Cl | H | O(CH$_2$)$_5$CH$_3$ | O | 82-83 |
| 182 | F | H | H | H | H | H | Cl | OCF$_2$CHF$_2$ | Cl | H | 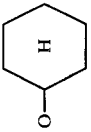 | O | 131-133 |
| 183 | F | H | H | H | H | H | Cl | OCF$_2$CHFCF$_3$ | Cl | H | OC$_2$H$_5$ | O | 105 |
| 184 | Cl | H | H | H | H | H | Cl | OCF$_2$CHFCF$_3$ | Cl | H | OC$_2$H$_5$ | O | 103-105 |
| 185 | F | H | H | H | F | H | Cl | OCF$_2$CHFCF$_3$ | Cl | H | OC$_2$H$_5$ | O | 94-97 |
| 186 | Cl | H | H | H | Cl | H | Cl | OCF$_2$CHFCF$_3$ | Cl | H | OC$_2$H$_5$ | O | 103 |
| 187 | F | H | H | H | F | H | Cl | OCF$_2$CHFCF$_3$ | Cl | H | OC$_2$H$_5$ | O | 90-91 |
| 188 | F | H | H | H | H | H | Cl | OCH$_2$CF$_3$ | Cl | H | OC$_2$H$_5$ | O | 101 |
| 189 | F | H | H | H | H | H | Cl | 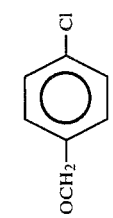 | Cl | H | OC$_2$H$_5$ | O | 143-145 |
| 190 | F | H | H | H | F | H | Cl | O—C=CH<br>    \|   \|<br>    Cl  Cl | Cl | H | OC$_2$H$_5$ | O | oil |
| 191 | F | H | H | H | F | H | Cl | SCHF$_2$ | Cl | H | OC$_2$H$_5$ | O | oil |
| 192 | F | H | H | H | H | H | Cl | 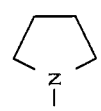 | Cl | H | OC$_2$H$_5$ | O | 93-95 |
| 193 | F | H | H | H | F | H | Cl | COO(CH$_2$)$_6$CH$_3$ | Cl | H | OC$_2$H$_5$ | O | oil |
| 194 | Cl | H | H | H | H | H | CH$_3$ | OCF$_2$CHF$_2$ | CH$_3$ | H | OC$_2$H$_5$ | O | 111-112 |

-continued
B. Chemical Examples

| Example No. | R¹ | R² | R³ | R⁴ | R⁵ | R⁶ | R⁷ | R⁸ | R⁹ | R¹⁰ | X | Y | M.P. (°C.) of E/Z-mixture |
|---|---|---|---|---|---|---|---|---|---|---|---|---|---|
| 195 | F | H | H | H | H | F | Cl | F | Cl | H | OC₂H₅ | O | 125-126 |
| 196 | Cl | H | H | H | H | F | Cl | F | Cl | H | OC₂H₅ | O | 113-114 |
| 197 | F | H | H | H | Cl | F | Cl | F | Cl | H | OC₂H₅ | O | 98-99 |
| 198 | Cl | H | H | H | Cl | F | Cl | F | Cl | H | OC₂H₅ | O | 115-116 |
| 199 | F | H | H | H | H | Cl | F | F | F | H | OC₂H₅ | O | 127-128 |
| 200 | F | H | H | H | H | Cl | CHF₂ | Cl | CF₃ | H | OC₂H₅ | O | 148 |
| 201 | Cl | H | H | H | H | Cl | CHF₂ | Cl | CF₃ | H | OC₂H₅ | O | 103 |
| 202 | F | H | H | H | Cl | Cl | CHF₂ | Cl | CF₃ | H | OC₂H₅ | O | 81-86 |
| 203 | Cl | H | H | H | Cl | Cl | CHF₂ | Cl | Cl | H | OC₂H₅ | O | 124 |
| 204 | F | H | H | H | H | Cl | Cl | Cl | Cl | H | OC₂H₅ | O | 140 |
| 205 | Cl | H | H | H | H | Cl | Cl | Cl | Cl | H | OC₂H₅ | O | 147 |
| 206 | F | H | H | H | Cl | Cl | Cl | Cl | Cl | H | OC₂H₅ | O | 165 |
| 207 | Cl | H | H | H | Cl | Cl | Cl | Cl | Cl | H | OC₂H₅ | O | 172 |
| 208 | F | H | H | H | F | CH₃ | CH₃ | OCF₂CHF₂ | CH₃ | H | OC₂H₅ | O | oil |
| 209 | Cl | H | H | H | H | F | F | H | F | F | OC₂H₅ | O | 161 |
| 210 | F | H | H | H | H | F | F | H | F | F | OC₂H₅ | O | 150 |
| 211 | Cl | H | H | H | Cl | F | F | F | F | F | OC₂H₅ | O | 125-128 |
| 212 | F | H | H | H | H | F | F | F | F | F | OC₂H₅ | O | 122 |
| 213 | Cl | H | H | H | H | F | F | F | F | F | OC₂H₅ | O | 110 |
| 214 | F | H | H | H | Cl | F | F | F | F | F | OC₂H₅ | O | 143 |
| 215 | Cl | H | H | H | Cl | F | F | F | F | F | OC₂H₅ | O | 150 |

The preparation of the compounds listed above is effected in accordance with one of the instructions given below.

Each process variant is illustrated by means of an Example in the Table.

Process variant (a)—Preparation of the compound according to Example No. 14

8.36 g (50 mmol) of ethyl 2-fluorobenzcarboximidate and 6.14 g (50 mmol) of p-chlorophenyl isocyanate were stirred for 4 hours at 20° C. 20 ml of n-hexane were then added and the solid was filtered off with suction, washed with n-hexane and dried.

Yield: 14.3 g (89%); Melting point: 130°-132° C.

Process variant (b)—Preparation of the compound according to Example No. 71

6.45 g (40 mmol) of p-trifluoromethylaniline were added dropwise to 9.19 g (40 mmol) of ethyl N-(chlorocarbonyl)-2-fluorobenzcarboximidate and 4.05 g (40 mmol) of triethylamine in 50 ml of absolute methylene chloride, and the mixture was stirred for 6 hours at room temperature. The organic phase was washed with water, dried with $MgSO_4$ and evaporated on a rotary evaporator, and the residue was recrystallized from n-hexane.

Yield: 12.0 g (85%); Melting point: 131° C.

Proces variant (c)—Preparation of the compound according to Example No. 33

11.95 g (30 mmol) of 6-(2,6-difluorophenyl)-3-(4-trifluoromethoxyphenyl)-1,2,3,4-tetrahydro-2H,4H-1,3,5-oxadiazine-2,4-dione and 100 mg of sodium methylate in 50 ml of absolute ethanol were boiled under reflux for 4 hours, cooled to room temperature and diluted with water, and the solid which had been precipitated was filtered off with suction, dried and crystallized from n-hexane.

Yield: 5 g (43%); Melting point: 90°-93° C.

C. BIOLOGICAL EXAMPLES

Example I

Spodoptera test

Larvae of the African cotton worm (*spodoptera littoralis* L III) and petri dishes into which a diet based on agar had been placed were treated in a spray apparatus with a preparation of the active compound at the desired concentration. After the spray coating had dried on, the larvae were placed on the agar diet.

After the desired time (L III up to hatching of butterflies) the mortality of the caterpillars or the hatching of the butterflies was determined as a %. In this case 100% denotes that all the caterpillars have been destroyed or that no butterflies hatched out of the caterpillars.

In this test, using a concentration of active compound of 0.001%, compounds Nos. 16, 18, 20, 22, 23, 24, 29, 31, 33, 37, 40, 42, 71, 93, 102, 106, 107, 108, 109, 119, 123, 152, 153, 154, 155, 156, 157, 158, 159, 162, 163, 165, 167, 170, 183, 184, 185, 186, 195, 196, 197, 201 and 205 exhibited a 100% action.

Example II

Musca test

Larvae of house flies, 24 hours old (*Musca domestica*), were placed in a fly diet which had previously been treated with an active compound preparation of the desired concentration.

After the desired time (L I up to hatching of flies) the mortality of the larvae or the hatching of the flies was determined as a %. In this case 100% denotes that all the larvae had been destroyed or that no flies hatched out of the pupae.

In this test, using a concentration of active compound of 0.01%, compounds Nos. 20, 23, 29, 33, 40, 42, 56, 60, 71, 73, 81, 82, 89, 106, 107, 109, 110, 111, 118, 119, 131, 135, 150, 153, 154, 155, 158, 159, 163, 174, 184, 185, 195, 196, 197 and 215 exhibited a 100% degree of action.

Example III

Aedes test

The aqueous preparations of active compound at the desired concentration were put into conical flasks and larvae, 24 hours old, of yellow fever mosquitoes (*Aedes aegypti*) were then put into the flasks.

After the desired time (up to hatching of mosquitoes) the mortality of the larvae or the hatching of the mosquitoes was determined as a percentage. In this case 100% denotes that all the larvae had been destroyed or that no mosquitoes hatched out.

In this test, using a concentration of active compound of 0.001%, compounds Nos. 3, 4, 9, 10, 14, 18, 20, 21, 23, 28, 29, 31, 33, 37, 40, 41, 42, 50, 51, 55, 56, 58, 60, 61, 62, 71, 72, 80, 81, 82, 93, 103, 106, 111, 114, 116, 119, 126, 127, 131, 135, 137, 138, 139, 142, 143, 144, 146, 153, 154, 155, 158, 159, 162, 163, 165, 167, 169, 170, 173, 179, 180, 182, 184, 185, 187, 195, 196, 197 and 204 exhibited a 100% action.

Example IV

Epilachna test

Larvae of the Mexican bean beetle (*Epilachna varivestis* L III) were treated in a spray apparatus with a preparation of the active compound at the desired concentration. At the same time leaves of bush beans (*Phaseolus vulgaris*) were immersed in the appropriate solution of active compound. After the spray coating had dried on, the larvae of the beetle were placed on the bean leaves.

After the desired time (L III up to hatching of beetles), the mortality of the larvae or the hatching of the beetles was determined as a %. In this case, 100% denotes that all the larvae had been destroyed or that no beetles hatched out of the pupae.

In this test, using a concentration of active compound of 0.1%, compounds Nos. 4, 9, 20, 23, 29, 33, 37, 42, 51, 55, 71, 72, 81, 83, 84, 94, 103, 119 and 131 exhibited a 100% degree of action.

Example V

Oncopeltus test

Larvae of a cotton bug (*Oncopeltus fasciatus* L III) were put into a plastic beaker together with a dental pellet which had previously been treated with a preparation of active compound at the desired concentration.

After the desired time (L III up to imago), the mortality of the larvae or the hatching of the imagos was determined as a %. In this case 100% denotes that all the larvae had been destroyed or that no imagos hatched out of the last larval stage.

In this test, using a concentration of active compound of 0.1%, compounds Nos. 23, 29, 33, 37 and 72 exhibited a 100% mortality.

We claim:
1. A compound of the formula I

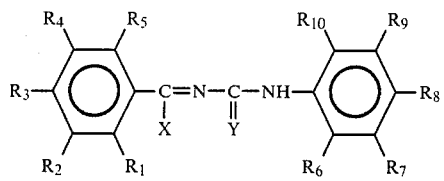

wherein $R_1$ is hydrogen, fluorine or chlorine, $R_2$, $R_3$ and $R_4$ are hydrogen, $R_5$ is fluorine or chlorine, $R_6$ and $R_{10}$ are hydrogen, $R_8$ is halogenated $(C_1-C_6)$-alkoxy or halogenated $(C_1-C_6)$-alkylmercapto, $R_7$ and $R_9$ are chlorine, X is $(C_1-C_6)$-alkoxy and Y is oxygen.

2. The compound as claimed in claim 1 wherein $R_8$ is selected from the group consisting of $OCF_2CHF_2$, $OCF_2CHCl_2$, $OCF_2CHClF$, $OCF_2CHBrF$ or $OCF_2CHFCF_3$ and X is $(C_1-C_4)$-alkoxy.

3. The compound as claimed in claim 1, which is O-ethyl N-[N-(3,5-dichloro-4-(2-chloro-1,1,2-trifluoroethoxy)-phenyl)-carbamoyl]-2,6-difluorobenzcarboximidate.

4. The compound as claimed in claim 1, wherein $R_8$ is halogenated $(C_1-C_6)$-alkylmercapto.

5. The compound as claimed in claim 1, which is O-ethyl N-[N-(3,5-dichloro-4-(1,1,2,2-tetrafluoroethoxy)-phenyl)-carbamoyl]-2-fluorobenzcarboximidate.

6. The compound as claimed in claim 1, which is O-ethyl N-[N-(3,5-dichloro-4-(1,1,2,2-tetrafluoroethoxy)-phenyl)-carbamoyl]-2,6-difluorobenzcarboximidate.

7. The compound as claimed in claim 1, which is O-ethyl N-[N-(3,5-dichloro-4-(1,1,2,3,3,3-hexafluoro-1-propoxy)-phenyl)-carbamoyl]-2-fluorobenzcarboximidate.

8. The compound as claimed in claim 1, which is O-ethyl N-[N-(3,5-dichloro-4-(1,1,2,3,3,3-hexafluoro-1-propoxy)-phenyl)-carbamoyl]-2-chlorobenzcarboximidate.

9. The compound as claimed in claim 1, which is O-ethyl N-[N-(3,5-dichloro-4-(1,1,2,3,3,3-hexafluoro-1-propoxy)-phenyl)-carbamoyl]-2,6-difluorobenzcarboximidate.

* * * * *